(12) United States Patent
Shah

(10) Patent No.: US 7,329,874 B2
(45) Date of Patent: *Feb. 12, 2008

(54) $LU_{1-X}I_3$:$CE_X$-A SCINTILLATOR FOR GAMMA-RAY SPECTROSCOPY AND TIME-OF-FLIGHT PET

(75) Inventor: Kanai S. Shah, Newton, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 110 days.

This patent is subject to a terminal disclaimer.

(21) Appl. No.: 11/271,053

(22) Filed: Nov. 10, 2005

(65) Prior Publication Data

US 2006/0124854 A1 Jun. 15, 2006

Related U.S. Application Data

(63) Continuation-in-part of application No. 10/948,914, filed on Sep. 23, 2004, now Pat. No. 7,173,247.

(60) Provisional application No. 60/505,636, filed on Sep. 24, 2003.

(51) Int. Cl.
*G01T 1/166* (2006.01)
(52) U.S. Cl. .................. 250/363.03
(58) Field of Classification Search ........... 250/363.03; 252/301.4 R
See application file for complete search history.

(56) References Cited

U.S. PATENT DOCUMENTS

| | | |
|---|---|---|
| 3,978,337 A | 8/1976 | Nickles et al. |
| 4,337,397 A | 6/1982 | Vacher |
| 4,510,394 A | 4/1985 | Allemand et al. |
| 4,559,597 A | 12/1985 | Mullani |
| 4,563,582 A | 1/1986 | Mullani |
| 4,647,779 A | 3/1987 | Wong |
| 4,768,156 A | 8/1988 | Whitehouse et al. |
| 4,833,327 A | 5/1989 | Hart |
| 4,864,140 A | 9/1989 | Rogers et al. |
| 4,980,552 A | 12/1990 | Cho et al. |
| 5,039,858 A | 8/1991 | Anderson et al. |
| 5,134,293 A | 7/1992 | Anderson et al. |

(Continued)

FOREIGN PATENT DOCUMENTS

WO    WO 01/60945    8/2001

OTHER PUBLICATIONS

Allemand, R. et al., "Potential advantages of a cesium fluoride scintillator for a time-of-flight positron camera," *J. Nucl. Med.*, 21:153-155 (1980).

(Continued)

*Primary Examiner*—Constantine Hannaher
(74) *Attorney, Agent, or Firm*—Townsend and Townsend and Crew LLP

(57) ABSTRACT

The present invention includes very fast scintillator materials including lutetium iodide doped with Cerium ($Lu_{1-x}I_3$:$Ce_x$; $LuI_3$:Ce). The $LuI_3$ scintillator material has surprisingly good characteristics including high light output, high gamma-ray stopping efficiency, fast response, low cost, good proportionality, and minimal afterglow that the material is useful for gamma-ray spectroscopy, medical imaging, nuclear and high energy physics research, diffraction, non-destructive testing, nuclear treaty verification and safeguards, and geological exploration.

37 Claims, 16 Drawing Sheets

U.S. PATENT DOCUMENTS

| | | | |
|---|---|---|---|
| 5,151,599 | A | 9/1992 | Monnet et al. |
| 5,159,195 | A | 10/1992 | Van House |
| 5,272,343 | A | 12/1993 | Stearns |
| 5,272,344 | A | 12/1993 | Williams |
| 5,319,203 | A | 6/1994 | Anderson et al. |
| 5,326,974 | A | 7/1994 | Karras et al. |
| 5,453,623 | A | 9/1995 | Wong et al. |
| 5,532,489 | A | 7/1996 | Yamashita et al. |
| 5,665,971 | A | 9/1997 | Chen et al. |
| 5,821,541 | A | 10/1998 | Tumer |
| 5,841,140 | A | 11/1998 | Mc Croskey et al. |
| 6,072,177 | A | 6/2000 | Mc Croskey et al. |
| 6,236,050 | B1 | 5/2001 | Tumer |
| 6,255,655 | B1 | 7/2001 | Mc Croskey et al. |
| 6,362,479 | B1 | 3/2002 | Andreaco et al. |
| 6,420,711 | B2 | 7/2002 | Tumer |
| 6,448,560 | B1 | 9/2002 | Tumer |
| 7,173,247 | B2 * | 2/2007 | Shah ............ 250/363.03 |
| 2005/0104001 | A1 | 5/2005 | Shah |
| 2005/0188914 | A1 * | 9/2005 | Iltis et al. ............ 117/2 |

OTHER PUBLICATIONS

Bollinger, L. and Thomas, G., "Measurement of the time dependence of scintillation intensity by a delayed-coincidence method," *Rev. Sci. Instrum.*, 32:1044-1050 (Sep. 1961).

Budinger, T., "Time-of-flight positron emission tomography: status relative to conventional PET," *J. Nucl. Med.*, 24:73-78 (Jan. 1983).

Burnham, C. et al., "New instrumentation for positron scanning," *International Conference on Radioisotopes in Localization of Tumors*, England, Sep. 25-27, 1967.

Dorenbos, P. et al., "Non-proportionality in the scintillation response and the energy resolution obtainable with scintillation crystals," *IEEE Trans. Nucl. Sci.*, 42:2190-2202 (Dec. 1995).

Gariod, R. et al., "The 'LETI' positron tomograph architecture and time of flight improvements," Workshop on Time-of-Flight Positron Tomography May 17-19 (1982), Washington University, St. Louis, Missouri, *IEEE Catalog* No. 82CH1719-3.

Guillot-Nöel, O. et al., "Scintillation properties of $RbGd_2Br_7$:Ce advantages and limitations," *IEEE Trans. Nucl. Sci.*, 46:1274-1284 (Oct. 1999).

Kaufman, L. et al., "Delay line readouts for high purity germanium medical imaging cameras," *IEEE Trans. Nucl. Sci.*, NS-21:652-657 (Feb. 1974).

Lewellen, TK, "Time-of-flight PET," *Semin. Nucl. Med.*, 28:268-275 (Jul. 1998).

Lewellen, TK et al., "Performance measurements of the SP3000/UW time-of-flight positron emission tomograph," *IEEE Trans. Nucl. Sci.*, 35:665-669 (Feb. 1988).

Moses, W. and Derenzo, S., "Scintillators for positron emission tomography," *Proceedings of SCINT '95*, Delft, The Netherlands, pp. 9-16 (1996).

Moses, W. et al., "Gamma ray spectroscopy and timing using LSO and PIN photodiodes," *IEEE Trans. Nucl. Sci.*, NS-42:597-600 (1995).

Moses, W. et al., "$LuAlO_3$:Ce—a high density, high speed scintillator for gamma detection," *IEEE Trans. Nucl. Sci.*, NS-42:275-279 (1995).

Moses, W. et al., "Performance of a PET detector module with LSO scintillator crystals and photodiode readout," *J. Nucl. Med.*, 37:85P (1996).

Moses, W. and Derenzo, S., "Prospects for time-of-flight PET using LSO scintillator," *IEEE Trans. Nucl. Sci.*, NS-46:474-478 (1999).

Mullani, N. et al., "Dynamic imaging with high resolution time-of-flight PET camera—TOFPET I," *IEEE Trans. Nucl. Sci.*, NS-31:609-613 (Feb. 1984).

Phelps, M., "Positron emission tomography provides molecular imaging of biological processes," *PNAS*, 97:9226-9233 (Aug. 1, 2000).

Weber, M. et al., "Dense $Ce^{3+}$-activated scintillator materials," *Proceedings of SCINT '95*, Delft, The Netherlands, pp. 325-328 (1996).

Wong, W. et al., "Characteristics of small barium fluoride (BaF) scintillator for high intrinsic resolution time-of-flight positron emission tomography," *IEEE Trans. Nucl. Sci.*, NS-31:381-386 (Feb. 1984).

Yamamoto, M. et al., "Time-of-flight positron imaging and the resolution improvement by an interactive method," *IEEE Trans. Nucl. Sci.*, 36(1):998-1002 (Feb. 1989).

Detko, J.F., "Operation characteristics of a small ultra-pure germanium gamma camera," *Semiconductor Detectors in Medicine*, Mar. 8-9, 1973, U.S. Atomic Energy Commission Office of Information Services Technical Information Center.

Shah, K.S., et al., "$LaBr_3$:Ce scintillators for gamma-ray spectroscopy," *IEEE Transactions on Nuclear Science* 50:2410-2413 (2003).

\* cited by examiner

LU$_{1-X}$I$_3$:CE$_X$-A SCINTILLATOR FOR GAMMA-RAY SPECTROSCOPY AND TIME-OF-FLIGHT PET

CROSS-REFERENCES TO RELATED APPLICATIONS

This application is a continuation-in-part of U.S. patent application Ser. No. 10/948,914, filed Sep. 23, 2004, now U.S. Pat. No. 7,173,247 and claims the benefit of U.S. Provisional Patent Application No. 60/505,636, filed Sep. 24, 2003, both of which are incorporated herein by reference in their entirety.

STATEMENT AS TO RIGHTS TO INVENTIONS MADE UNDER FEDERALLY SPONSORED RESEARCH OR DEVELOPMENT

Aspects of this research were conducted with finding provided by the Department of Energy and the National Institute of Health. Contract No. DE-AC03-76SF00098 and Grant Nos. R01-CA6791 1 and P01-HL25840, respectively. The United States Government may have certain rights in the application.

BACKGROUND OF THE INVENTION

The present invention relates generally to scintillators. More specifically, the present invention provides lutetium iodide (LuI) scintillators for use with medical imaging scanner systems, such as gamma ray spectroscopy and time-of-flight positron emission tomography.

Scintillators are the most widely used detectors for spectroscopy of energetic photons (X-rays and gamma-rays). These detectors are commonly used in nuclear and high energy physics research, medical imaging, diffraction, non-destructive testing, nuclear treaty verification and safeguards, and geological exploration. Important requirements for the scintillation crystals used in these applications include high light output, high gamma ray stopping efficiency (attenuation), fast response, low cost, good proportionality, and minimal afterglow. These requirements have not been met by any of the commercially available scintillators, and there is continued interest in the search for additional scintillators with enhanced performance.

One form of medical imaging is called positron emission tomography and is better known by its acronym PET. PET is a functional imaging technique used clinically and in research to quantify the rates of biological processes in vivo. See J. T. Bushberg, J. A. Seibert, E. M. Leidholdt, and J. M. Boone, The Essential Physics of Medical Imaging, Williams and Wilkins, (1994). The availability of short lived positron-emitting isotopes of carbon, nitrogen, oxygen and especially fluorine allows virtually any compound of biological interest to be labeled in trace amounts and introduced into the body for imaging with PET. The distribution of the tracer is imaged dynamically, allowing the rates of biological processes to be calculated using appropriate mathematical models. PET imaging can provide diagnosis for symptoms of diseases such as cancer, Alzheimer's disease, head trauma, and stroke. Phelps, M. E, "Positron emission tomography provides molecular imaging of biological processes", *Proc. Natl. Acad. Sc.i USA*, 97(16), 9226-9233, (2000).

In PET (or PET scan), the patient is injected with a molecule labeled with a positron-emitting radioactive element. In some applications the radiotracer is distributed through the body, and concentrated in (or excluded from) target tissues of interest. The radioactive material decays by emission of a positron, or antiparticle of the negatively-charged electron. The positron is slowed down within a short distance from the emission point and forms a short-lived "atom" consisting of the positron and an electron from a nearby atom. The "atom," referred to as positronium, decays by the annihilation of its constituents. This annihilation produces two essentially back to back 511 keV gamma-rays. When both of the gamma-rays are detected by detectors surrounding the body, it can be assumed with high probability that the emission point was somewhere along a line joining the two detectors. Without additional information, the probability that the radiotracer was located on any one point in the body that the detection line intersects is equal for all points in the line, and hence, for all points in the body being scanned.

A variety of algorithms have been developed that make it possible to form an image from a collection of such lines. The quality of the image improves, in general, as the number of lines increases. Similarly, as the signal-to-noise of the image depends on the square root of the number of lines, each line representing one annihilation event, more lines offer an improved signal-to-noise ratio. Nevertheless, a common aspect of all image formation or reconstruction algorithms is that the noise increases in the process of deciding where along the detected line the annihilation event is likely to have occurred. In one aspect, this effect can be thought of in terms of energy and work: The detected lines represent the energy in the image and a large part of that energy is used up as work in localizing the annihilation along the particular line, instead of contributing to image quality. If the body cross-section is 30 cm and the desired localization accuracy of an annihilation event is 5 mm, localization requires reducing the uncertainty of its location by a factor of 60.

The annihilation gamma-rays travel at a speed of about 30 cm/nanosecond (1 foot/ns). The timing accuracy of detectors currently used commercially in PET cameras is a few nanoseconds (ns). Timing resolution is typically applied to two aspects of PET: One use is to reduce accidentals (the overlapped detection of two unrelated gamma-rays). The other use is in timing signals for localization purposes. While any improvement in time resolution aids in accidentals reduction, until the time resolution drops substantially below about 1 ns, greater time resolution will not help in localization of an annihilation event within a target of about 30 cm—the more common presentation in human-PET scanning. That is, if a body cross-section is about 30 cm, that very fact localizes the event without any recourse to time resolution. With that limitation, an improvement in localization from 4 ns (4 feet) to 1 ns (1 foot) offers no improvement to image quality. On the other hand, a timing signal improvement from 1 ns to 500 picosecond (0.5 ns) reduces the uncertainty of event location by a factor of 2. To appreciate the value of this particular improvement, it is to be noted that the factor of 2 increase in time resolution accuracy results in a corresponding increase in signal-to-noise ratio. This results in the equivalent of a factor of 4 increase in detected annihilation events. Placed in a different context, under the same circumstances, an image (actually a data set) that may take 15 minutes to obtain with a 1 ns time resolution, is obtained in under about 4 minutes when the time resolution is 500 ps.

FIG. 1 illustrates the principle on which the location along the detected line is used to improve image formation.

PET is playing a prominent and an increasingly visible role in modern research and clinical diagnosis. However, there is a need for improvement in PET instrumentation in order to exploit the full potential of this promising technique. The performance of current PET systems is limited by the available detector technology. Scintillation crystals (herein referred to a "scintillators") coupled to photomultiplier tubes are commonly used as detectors in PET systems. Important requirements for the scintillators used in PET systems include fast response, high sensitivity, high light output, high energy and timing resolution, and low cost. High energy resolution is important because it allows rejection of scattered events. High timing resolution is important because it allows rejection of random events. Furthermore, if sufficiently fast scintillators become available, time-of-flight (TOF) information could be utilized to obtain better event localization compared to conventional PET, which can lead to enhanced signal-to-noise ratio in the reconstructed image. Budinger T F, "Time-of-flight positron emission tomography: status relative to conventional PET", *J. Nucl. Med.* 24: 73-78, (1983).

It is generally recognized that a fast timing scintillator in PET cameras will enable time-of-flight PET when the timing accuracy and/or timing resolution is below 1 ns. Hitherto no true time-of-flight PET device has been enabled. Barium fluoride ($BaF_2$), lutetium orthosilicate (LSO) and bismuth germanate (BGO) have been suggested as potentially useful scintillation materials, but none of these materials has the 500 picosecond (ps) or less time resolution needed to achieve a successful device. BGO, however, has a poor energy resolution and slow response, which limits its performance in 3D whole body imaging. The energy resolution of LSO is variable and is limited by its non-proportionality. Moses W W, *Current Trends in Scintillator Detectors and Materials*, Nucl. Inst. And Meth., A 487, p. 123-128, (2002). $BaF_2$ actually provides a ~250 ps (FWHM) timing resolution, but it has a low emission intensity for the fast component and emits in the blue region of the spectrum where special photomultiplier tubes (PMTs) with quartz windows are required for readout. It is noted that a number of plastic scintillators have a time resolution below 500 ps, but due to inadequate stopping power, (attenuation length at 500 keV is typically greater than 10 cm), these scintillators are not suitable for medical uses.

The present invention provides a cerium doped rare-earth halide scintillator, lutetium iodide ($Lu_{1-x}I_3:Ce_x$). The crystals provide a very fast scintillator material capable of resolving the position of an annihilation event within a portion of a human body cross-section (less than 400 ps). Specifically, the very fast scintillator material comprises $LuI_3$ doped with various concentrations of cerium. Crystals of this material have been grown and characterized and they provide scintillators with properties suitable for many uses including use as a gamma-ray detector, in nuclear and particle physics, X-ray diffraction, non-destructive evaluation, treaty verification and non-proliferation monitoring, environmental cleaning, geological exploration and medical imaging. The timing resolution measured for the $LuI_3:Ce$ crystals of the present invention demonstrate that the compositions provide a scintillator particularly useful in PET, including Time-of-Flight (TOF) PET devices and methods.

Attention is drawn to several references in the field, the teachings of which are incorporated herein by reference (as are all references cited herein):

U.S. Pat. No. 6,362,479, "Scintillation detector array for encoding the energy, position, and time coordinates of gamma ray interactions," discloses a scintillator-encoding scheme that depends on the differential decay time of various scintillators. The use of lutetium orthosilicate-lutetium orthosilicate (LSO-LSO) crystals with a time resolution of 1.6 ns is also discussed. A time resolution of 1.6 ns is equivalent to an approximately 50 cm uncertainty, which is as large as the cross-sectional dimension of the human body, and not useful in TOF-PET.

U.S. Pat. No. 5,453,623, "Positron emission tomography camera with quadrant-sharing photomultipliers and cross-coupled scintillating crystals." Discloses arrangement of hardware elements in PET camera and use of scintillators. Only specific scintillator disclosed is BGO.

Moses et al., "Prospects for Time-of-Flight PET using LSO Scintillator," *IEEE Trans. Nucl. Sci.* 46:474-478 (1999). Discloses measurements of the timing properties of lutetium orthosilicate (LSO) scintillator crystals coupled to a PMT and excited by 511 keV photons.

U.S. Pat. No. 5,319,203 and U.S. Pat. No. 5,134,293, both entitled "Scintillator material." Discloses Cerium fluoride and thallium doped Cerium fluoride as "improved" scintillator material.

U.S. Pat. No. 5,039,858, "Divalent fluoride doped cerium fluoride scintillator." Discloses additional doped cerium fluoride scintillators.

U.S. Pat. No. 4,510,394, "Material for scintillators." Discloses barium fluoride as scintillator material.

van Loef et al., "High energy resolution scintillator: $Ce^{3+}$ activated $LaBr_3$", *Appl. Phys. Lett.* 79:1573-1575 (2001).

van Loef et al., "Scintillation properties of $LaBr_3:Ce^{3+}$ crystals: fast, efficient and high-energy-resolution scintillators", *Nuc. Instr. Meth. Physics Res. A* 486:254-258 (2002). Discloses certain characteristics of cerium doped $LaBr_3$ compositions including, light yield, and scintillation decay curve. The rise time and time resolution of the compositions are not disclosed or suggested.

WO 01/60945, "Scintillator crystals, method for making same, use thereof", Discloses inorganic scintillator material of the general composition $M_{1-x}Ce_xBr_3$, where M is selected from lanthanides or lanthanide mixtures of the group consisting of La, Gd, and Y. X is the molar rate of substitution of M with cerium, x being present in an amount of not less than 0.01 mol % and strictly less than 100 mol %. The rise time and time resolution of the various compositions are not disclosed or suggested.

BRIEF SUMMARY OF THE INVENTION

The present invention provides a cerium doped lutetium iodide ($LuI_3:Ce$) scintillator. Crystals of $LuI_3:Ce$ have been manufactured using melt based Bridgman method. Scintillation properties of small $LuI_3:Ce$ crystals (~0.3 cm³, doped with $Ce^{3+}$) include a peak emission wavelength for $LuI_3:Ce$ at ~474 nm, and in some instances the peak can be found to be at ~470 nm, which is well matched to photomultiplier tubes (PMTs) as well as silicon diodes used in nuclear instrumentation.

The principal decay-time constant for $LuI_3:Ce$ (with 5% $Ce^{3+}$) is about 25 ns and, in some cases less than 25 ns, which is faster than the decay-time constant of commercial PET scintillators such as BGO, LSO, NaI:Tl and GSO. The principal decay-time constant for $LuI_3:Ce$ was measured to be $\leq 30$ ns over most of the $Ce^{3+}$ concentration ranges examined. The light output of $LuI_3:Ce$ is ~50,000 photons/MeV which is about 2 times higher than that of LSO, about 6-7 times higher than that for BGO and GSO, and about 31% higher than that of NaI:Tl, which is a slow scintillator. In some instances, the light output of $LuI_3:Ce$ was measured to be remarkably high, for example, ~100,000 photons/MeV, which is the highest reported value for scintillation materials. Thus, the light output of LuI$_3$:Ce is ~4 times higher than that for LSO, ~12 times higher than that for BGO, and ~2.6 times higher than that for NaI:Tl.

The initial photon intensity—a figure of merit for timing applications is also higher for LuI$_3$:Ce compared to BGO, LSO, NaI:Tl and GSO. The combination of higher light output and faster response for LuI$_3$.Ce compared to existing PET scintillators promises high energy and timing resolution with LuI$_3$:Ce scintillators. These properties are very attractive in whole body PET imaging where the ability to reject randoms and scatter needs to be improved. The timing resolution of a LuI$_3$:Ce crystal in coincidence with a BaF$_2$ crystal was measured to be 210 ps (FWHM) in initial analyses, and 195 ps (FWHM) in a further evaluation. Thus, LuI$_3$:Ce also provides the opportunity for time-of-flight (TOF) PET imaging which would provide an additional gain in signal to noise ratio and image quality.

Due to its high atomic number constituents and high density (5.6 g/cm$^3$), LuI$_3$:Ce provides high gamma-ray sensitivity. The mean penetration depth of 511 keV photons in LuI$_3$:Ce is about 1.7 cm, which is comparable to that for GSO and slightly larger than that for LSO and BGO. The mean penetration depth of LuI$_3$:Ce is substantially shorter than that for NaI:Tl. Furthermore, the energy resolution of LuI$_3$:Ce for 511 KeV gamma-rays has been measured at ~4% (FWHM) at room temperature, which is substantially better than that of all scintillators that are currently used in commercial PET scanners.

Since LuI$_3$ melts congruently, it can be grown using crystal growth techniques such as Bridgman and Czochralski which are generally easy to scale-up. Furthermore, the melting point of LuI$_3$ is 1050° C., which is substantially lower than the melting point of LSO and GSO (>2000° C.). As a result, the eventual cost of LuI$_3$:Ce can be expected to be considerably lower than that of LSO and GSO. This issue is particularly relevant in modern PET instrumentation where the high cost of the detector components can be a major limitation. Thus, LuI$_3$:Ce appears to be a very promising scintillator for PET imaging.

In one embodiment the present invention comprises a very fast scintillator comprising lutetium iodide and a trivalent cerium dopant. In one configuration, said dopant is present at about 0.1% or more and less than or equal to about 100% by molar weight (e.g., a CeI$_3$ scintillator), and particularly from about 0.5% to about 5%, or about 0.5% to about 20%, by molar weight, and more particularly about 0.5%, 5.0%, 10% or 20% by molar weight.

In certain embodiments the scintillator has a fast component with a decay constant of about 23 to about 31 nanoseconds. These embodiments also have a timing resolution of about 210 ps and about 195 ps, making the compositions useful for time-of-flight PET. Optionally, the scintillator may have a slow component with a decay constant of about 120 to about 230 nanoseconds.

In another aspect this invention comprises a positron emission scanner system comprising a patient area and an assembly of radiation detectors disposed adjacent the patient area. The radiation detectors comprise a fast scintillator comprising lutetium iodide and a trivalent cerium dopant. A scintillation light detector or photomultiplier tube are optically coupled to the scintillator. A control system is coupled to the light detectors or photomultiplier tube.

In one configuration, the dopant is present at about 0.1% or more and less than or equal to about 100% by molar weight, preferably between about 0.5% and about 20% by molar weight (e.g., about 0.5%, 5.0%, 10% or 20% by molar weight), or preferably between about 0.5% or more and less than or equal to about 5.0% by molar weight, and most preferably between about 2% and about 5.0% by molar weight. The compositions comprising lutetium iodide and a trivalent cerium dopant also have high light output, sufficient stopping power and energy and/or timing resolution required for a positron emission scanner system useful for time-of-flight measurements.

In some configurations, the scintillator is used in coincidence detection positron emission tomography by recording the differential arrival time of two photons so as to localize the annihilation event. Advantageously, the localization is carried out within a distance that is less than about 30 cm.

The positron emission tomography scanner typically includes two or more radiation detectors, in which each scintillation light detector of the radiation detector comprises a position sensitive detector or array. The scanner typically includes means to correct for different timing offsets of each of the individual radiation detectors. Such timing offsets of the individual radiation detectors are stored in a memory in the control system. For example, in one configuration, for each radiation detector the timing offsets are subtracted from each gamma-ray time arrival value prior to computation of a localization. In another configuration, timing signals of individual radiation detectors are equalized by an introduction of individual hardwired delays in signal readout electronics in the control system.

Optionally, the scanner, comprising two or more scintillators, uses Ce doped LuI$_3$ in combination with other scintillators.

In a further embodiment the present invention comprises an X-ray computed tomography (CT) scanner system comprising a patient area and a penetrating x-ray source. A detector assembly is positioned adjacent the patient area on a substantially opposite side of the patient area. The detector assembly comprises a scintillator comprising lutetium iodide and a trivalent cerium dopant.

In one embodiment, the dopant is typically present at about 0.1% or more and less than or equal to about 100% by molar weight, preferably between about 0.5% and about 20% by molar weight (e.g., about 0.5%, 5.0%, 10% or 20% by molar weight), or preferably between about 0.5% or more and less than or equal to about 5.0% by molar weight, and most preferably about 5.0% by molar weight. The cerium doped lutetium iodide fast scintillator also possess additional characteristics necessary for an X-ray CT scanner system, such as for example, high detection efficiency (high density and atomic number), high light output, linear light output with energy, fast decay time, low cost and ease of crystal fabrication.

An additional embodiment of the present invention is a method of performing time-of-flight positron emission tomography. Such methods use a scintillator comprising lutetium iodide (LuI$_3$) and trivalent cerium as a dopant. The scintillator typically has a fast component with a decay constant of about 23 to about 31 nanoseconds, and a time resolution of less than 500 picoseconds (ps), and preferably below 0.4 nanoseconds (ns). The scintillator may comprise a slow component with a decay constant of about 120 to about 230 nanoseconds.

The cerium dopant can be present at about 0.1% or more and less than or equal to about 100% by molar weight. More particularly, the cerium dopant is typically present at about 0.5% or more, preferably between about 0.5% and about 20% by molar weight (e.g., about 0.5%, 5.0%, 10% or 20% by molar weight), or preferably between about 0.5% and about 5.0% by molar weight, and most preferably between about 2.0% and about 5.0% by molar weight. The imaging method comprises injecting or otherwise administering to a patient a detectable label, and after a sufficient period of time to allow localization or distribution of the label, placing the patient within the field of view of the device. When a 511 keV gamma-ray is detected by any one first detector, the device opens a time window (no less than up to about 1 ns long for the whole body, but longer if the time resolution of the device is worse than 1 hs, e.g., 10 ns for one of the scanners described above). If another 511 keV event is detected within this time window at a second detector that is across the body from the first detector (or, in some embodiments, where each detector comprises position sensing built within it), the position within the detector and the detector's position are recorded, as well as the arrival times. Each positive pair defines a line. From the known body size, the length of the line need not be the distance between detectors, it can be just the size of the body cross-section along the line, this event is accepted as a coincidence. The position of the first and second detectors (or, in some configurations where each detector comprises position sensing built within it, the position within the detector and the detector's position) are recorded, as well as the arrival times.

If there is no Time-of-Flight (TOF) information, equal probability is assigned to each point on the line. The reconstruction of the image then proceeds by one of the dozens of algorithms known in the art. If TOF information is available, then the probability of origin of the event along the line can be represented as a Gaussian or similar distribution of width equal to the TOF FWHM, centered on the most probable point. Similar reconstruction algorithms, modified to take advantage of the TOF information can be used for reconstruction, and these modifications are also well known in the art.

In another embodiment, the present invention provides a method of localizing a positron annihilation event within a portion of a human body cross-section. In the method a positron emission tomography scanner (or camera) is used wherein the scanner comprises a scintillator comprising lutetium iodide ($LuI_3$) and trivalent cerium as a dopant.

The scintillator may have a fast component with a decay constant of about 23 to about 31 nanoseconds, a decay constant of about 120 to about 230 nanoseconds, an attenuation length of about 1.7 cm, a light output of about 47,000 to 50,000 photons/MeV or about 38,000 to about 100,000 photons/MeV, an initial photon intensity of about 1,200 photons/(ns×MeV), and a time resolution of about 0.210 nanoseconds or about 0.195 nanoseconds.

For a fuller understanding of the nature and advantages of the present invention, reference should be had to the ensuing detailed description taken in conjunction with the accompanying drawings. The drawings represent embodiments of the present invention simply by way of illustration. The invention is capable of modification in various respects without departing from the invention. Accordingly, the drawings and description of these embodiments are illustrative in nature, and not restrictive.

DETAILED DESCRIPTION OF THE INVENTION

Figure 1:
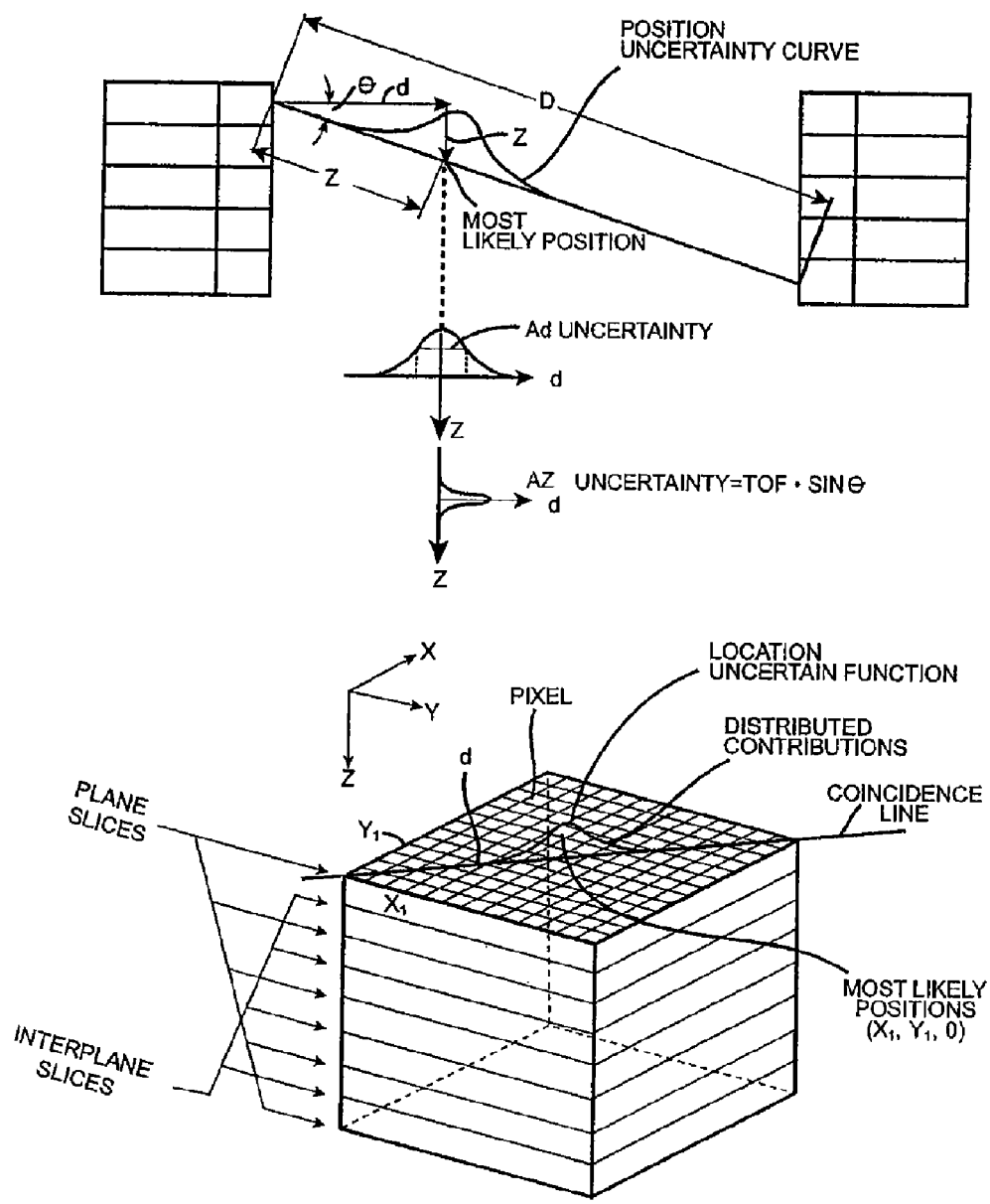
FIG. 1 illustrates the principle on which the location along the detected line is used to improve image formation.

This invention will be better understood with resort to the following definitions:

A. Rise time, in reference to a scintillation crystal material, shall mean the speed with which its light output grows once a gamma-ray has been stopped in the crystal. The contribution of this characteristic of a scintillator combined with the decay time contribute to a timing resolution. A timing resolution of less than 500 picosecond (ps) is of particular interest for use in methods comprising time-of-flight detection of an annihilation event as originating within about a 30 cm distance.

B. Fast timing scintillator should be capable of localizing an annihilation event as originating from within about a 30 cm distance, i.e., from within a human being scanned. This typically requires a timing resolution of about 500 ps or less.

C. Timing accuracy or resolution, usually defined by the full width half maximum (FWHM) of the time of arrival differences from a point source of annihilation gamma-rays. Because of a number of factors, there is a spread of measured values of times of arrival, even when they are all equal. Usually they distribute along a bell-shaped or Gaussian curve. The FWHM is the width of the curve at a height that is half of the value of the curve at its peak.

D. Light Output shall mean the number of light photons produced per unit energy deposited by the detected gamma-ray, typically the number of light photons/MeV.

E. Stopping power or attenuation shall mean the range of the incoming X-ray or gamma-ray in the scintillation crystal material. The attenuation length, in this case, is the length of crystal material needed to reduce the incoming beam flux to 1/e.

F. Proportionality of response (or linearity). For some applications (such as CT scanning) it is desirable that the light output be substantially proportional to the deposited energy.

G. Coincidence timing window/coincidence detection shall mean the length of time allowed for deciding whether two detected 511 keV gamma-rays belong to the same positron annihilation event. This window is desired to be as short as possible, but no shorter than the time it takes the gamma-rays to travel through the body (>1 nanosecond).

H. Single line time-of-flight (TOF) localization shall mean the process by which, through timing of the signals, the position of the annihilation event is localized to a portion of the line joining the detectors, this portion being smaller than the length of the body dimension along the line.

I. Position sensitive detector or array shall mean a detector where the position of the gamma-ray interaction within the detector is determined. In some embodiments this is done through the Anger principle of light division (well known in the state of the art). For instance, there can be a photodetector at each end of the crystal and the proportion of light reaching each detector determines position, or an array of photodetectors where the center of mass of the light distribution determines position (i.e., the closest detectors get more light).

J. Method to correct for different timing offsets of an individual detector shall be understood to include, among others, software code that stores each detector's individual timing delay and code to subtract from each timing signal this pre-stored value. Method to introduce through delay lines (cables through which the signal travels) a fixed delay for each detector, so that their signals all have the same arrival delay at the timing electronics.

Figure 2:
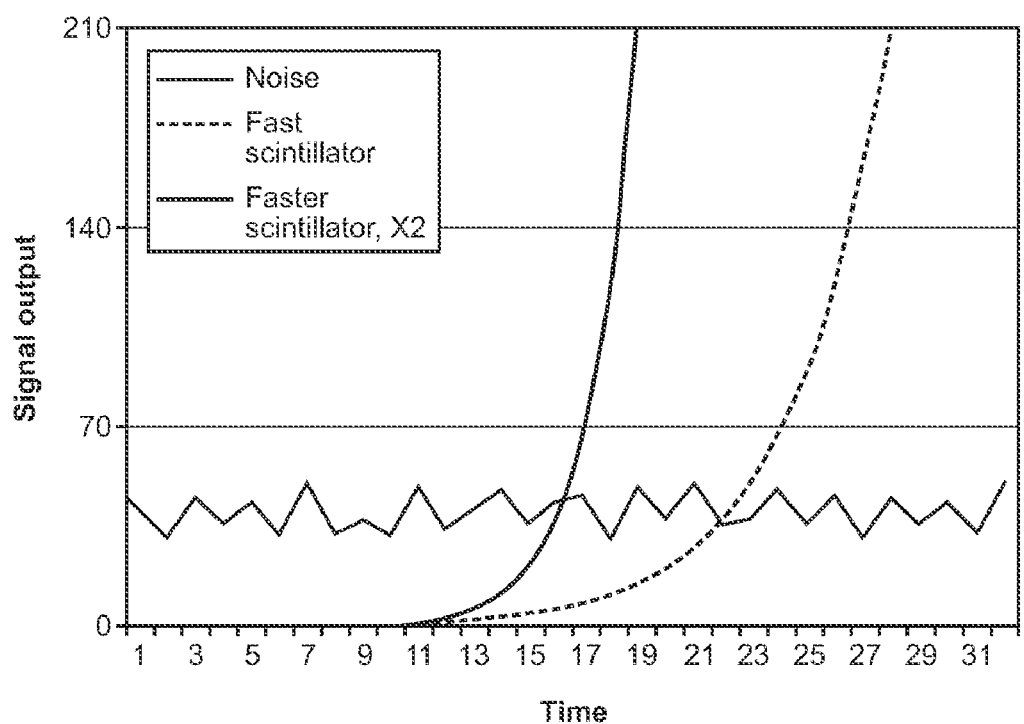
FIG. 2 represents output signals of two scintillators with the same light output, but one with a rise time speed twice as fast as the other.

A property of a scintillator crystal material is the speed with which its light output grows once a gamma-ray has been stopped in the crystal. This property is characterized by the rise time of the scintillator crystal. An example is shown in FIG. 2 for two scintillators with the same light output, but one with a rise time speed twice as fast as the other. There is a noise level (due to readout electronics) that does not allow the signal to be reliably detected until it exceeds a certain threshold (70 in this example). Both signals start at point 10 on the horizontal axis of the graph, and the faster scintillator crosses the threshold above noise faster. Consequently, variations in timing from different pulse strengths will be smaller for the faster rise time speed scintillator. The faster rise time scintillator permits a higher time resolution.

Figure 3:
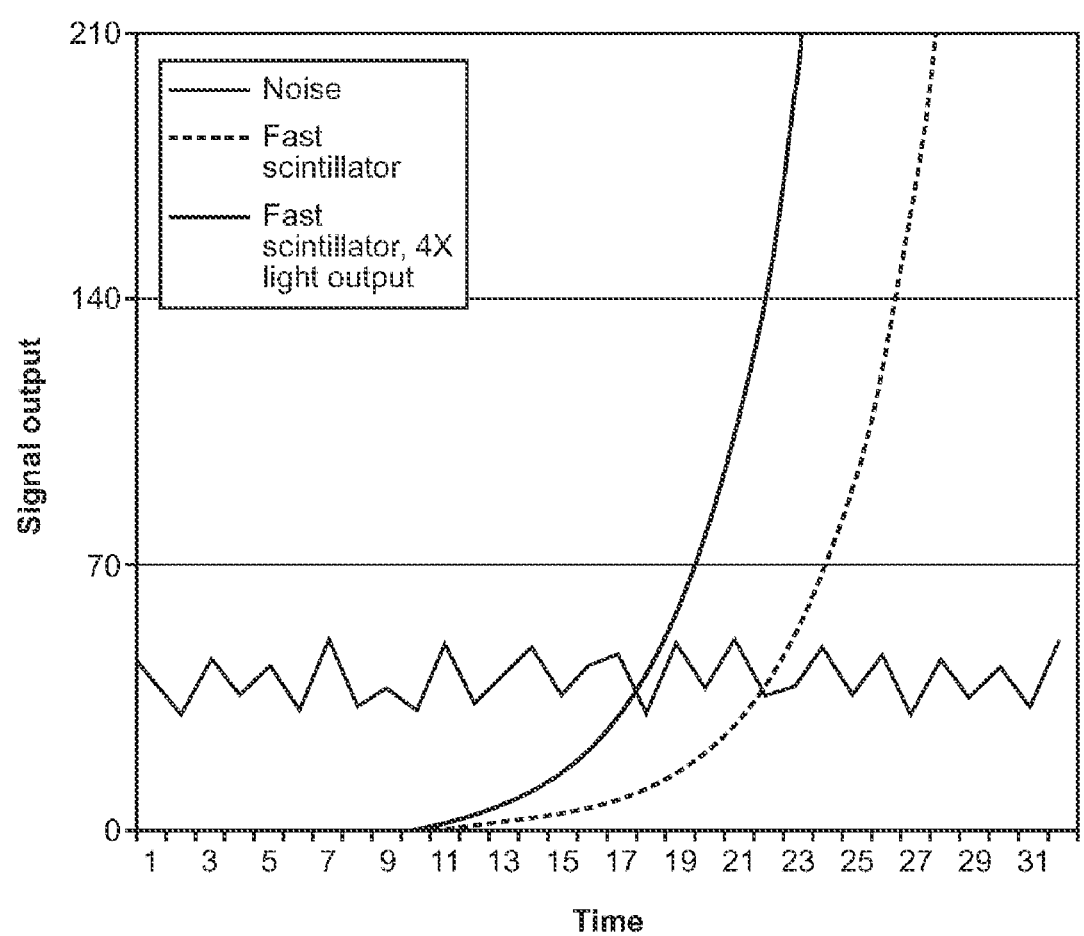
FIG. 3 shows the signal output from two scintillators of equal speed but different light output.

Increased or high light output impacts the signal-to-noise ratio in scintillation detection. Given the noise generally inherent in the readout electronics, higher light output leads to better energy resolution. Better energy resolution is useful in identifying and excluding gamma-ray detections of gamma-rays that have scattered in the body yielding a "false" line as compared with those that have not scattered. Higher light output also enables improved accuracy in timing. As the signal rises towards a higher peak value, it crosses a noise-dictated threshold of detectability sooner. As a result variations in signal output (due to finite energy resolution) lead to a smaller range of time differences in crossing the threshold. FIG. 3 shows the signal output from two scintillators of equal speed (rise time) but different light output.

Stopping power is an aspect of detection efficiency. Stopping power, particularly at 511 keV, is an important parameter for a scintillator material for use in a PET scanner or camera. This efficiency is dependent, in part, on the density and average atomic number of the scintillator material. High values of both density and average atomic number tend to increase detection or stopping power of the scintillator. A high stopping power is advantageous, and the higher, the better. The high attenuation power of $LuI_3$ (short attenuation length), means that physically smaller detectors can be built while maintaining good detection efficiency. Smaller detectors are understood by those familiar with the art as providing better time and spatial resolution.

In the practice of the present invention, attention is paid to the physical properties of the scintillator material. In most embodiments a robust scintillator crystal or ceramic is preferred. Similarly, in particular applications, properties such as hygroscopy (tendency to absorb water), brittleness (tendency to crack), and crumbliness should be minimal.

Table I below presents properties of two conventional positron scanners or cameras currently in the market. The time resolution of one of them, the TOFPET TTV 03, at 650 ps does not significantly localize an annihilation event within the typical 30 cm cross-section of a human. For such a time resolution, up to 40% of detected events can be localized to within 10 cm, and approximately 15% will appear to arise from outside a 30 cm body cross-section. A time resolution of 650 ps is not acceptable for use in PET TOF localization. A time resolution of less than 500 ps is required.

TABLE I

|  | TOFPET TTV 03 | PET Siemens/CTI |
| --- | --- | --- |
| Ring diameter (mm) | 890 | 820 |
| Number of rings | 4-6 | 24 |
| Number of detectors per ring | 324 | 784 |
| Crystal dimension (mm) | 7 × 18 × 45 | 2.9 × 5.9 × 30 |
| Type of crystal | $BaF_2$ | BGO |
| Spatial resolution (mm) | 5 | 4 |
| Time resolution (ps) | 650 | 750 |

Figure 9:
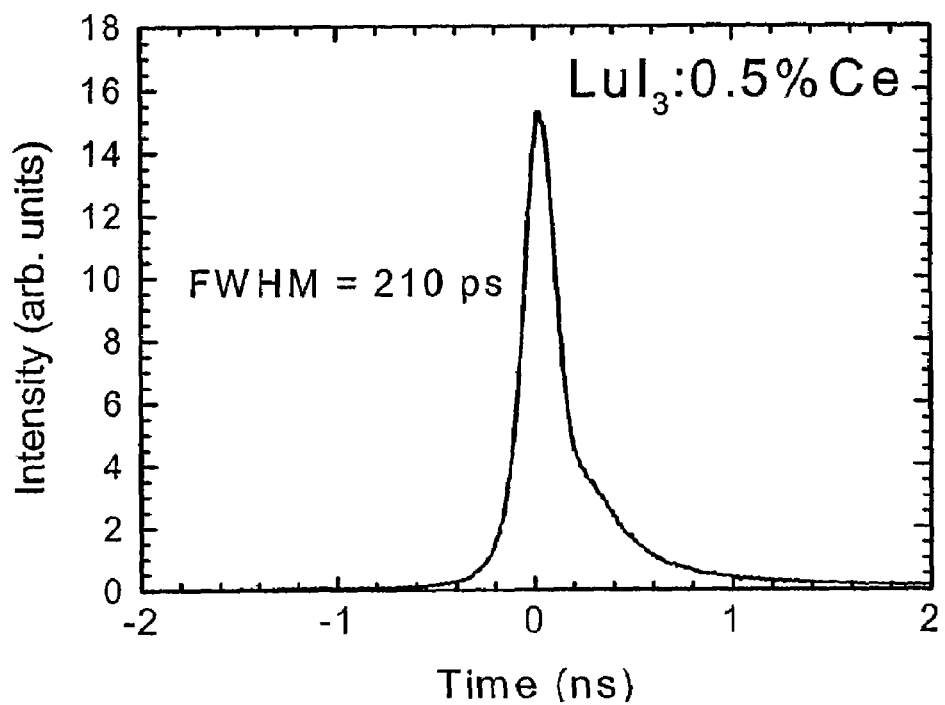
FIG. 9 provides the coincidence timing resolution plot for $BaF_2$ and $LuI_3$:Ce (0.5% Ce concentration) scintillators upon irradiation with 511 keV gamma-ray pairs. The timing resolution is 210 ps (FWHM).

The present invention includes a method of appropriately doping $LuI_3$ with trivalent Ce, to obtain a material capable of high light output (greater than about 50,000 photons/MeV at room temperature) well matched to photo-detection (FIG. 4), fast response (FIGS. 5 and 9) and to time-of-flight positron detection localization capabilities (time resolution of less than 500 ps; FIG. 9). $LuI_3$ doped with $Ce^{3+}$ at a concentration of about >0.1% $Ce^{3+}$ molar weight, and particularly concentrations between about 0.5% and about 5.0%, between about 0.5% and about 20%, and up to 100%, have been found to be useful in medical imaging including PET and time-of-flight positron detection localization, and the like.

TABLE II

Properties of Scintillators

| Material | Light Output (Photons/MeV) | Wavelength of Emission (nm) | Attenuation Length (511 keV) (cm) | Initial Photon Intensity (Photons/ (ns × MeV)) | Principal Decay Time (ns) |
|---|---|---|---|---|---|
| NaI(Tl) | 38,000 | 415 | 3.3 | 165 | 230 |
| CsI(Tl) | 52,000 | 540 | 1.9 | 50 | 1000 |
| LSO | 24000 | 420 | 1.2 | 600 | 40 |
| BGO | 8,200 | 505 | 1.1 | 30 | 300 |
| BaF$_2$ | 10,000~ 2,000 fast | 310 slow 220 fast | 2.3 | 3,400 (total) | 620 slow 0.6 fast |
| GSO | 7,600 | 430 | 1.5 | 125 | 60 |
| CdWO$_4$ | 15,000 | 480 | 1.1 | 3 | 5000 |
| YAP | 20,000 | 370 | 2.1 | 570 | 26 |
| LaBr$_3$ (0.5% Ce)[1] | 61,000 | 360 | 2.1 | 1,850 | 31 |
| LaBr$_3$ (0.5% Ce)[2] | 68,000 | 370 | 2.1 | 2,600 | 26 |
| LaBr$_3$ (5% Ce)[2] | 62,500 | 370 | 2.1 | 4,300 | 16 |
| LaBr$_3$ (10% Ce)[2] | 64,500 | 370 | 2.1 | 3,900 | 16 |
| LaBr$_3$ (20% Ce)[2] | 64,000 | 375 | 2.1 | 3,600 | 17 |
| LaBr$_3$ (30% Ce)[2] | 69,500 | 375 | 2.1 | 3,650 | 18.6 |
| LuI$_3$ (0.5% Ce) | 47,000 | 470 | 1.7 | 1,300 | 31 |
| LuI$_3$ (5% Ce)[3] | 50,000 | 474 | 1.7 | 1,800 | 25 |
| LuI$_3$ (5% Ce)[4] | 100,000 | 474 | 1.7 | 3,500 | 25 |

[1]Data based on the Delft University of Technology results (See, van Loef et al., Nucl. Inst. Meth. Phys. Res. A 486: 254-258 (2002)).
[2]Data and results provided in U.S. patent application Ser. No. 10/948,913, filed Sep. 23, 2004; Attorney Docket No. 22071-000110US.
[3]Data from Example 2 herein.
[4]Data from Example 3 herein.

Compared to CsI, which is among the scintillation materials with the highest known light output, LuI$_3$ produces about the same amount of light (approximately 47,000 to about 50,000 photon/MeV - see, e.g., Example 2) or more (approximately 38,000 to about 100,000 photon/MeV—see, e.g., Example 3), a fast principal decay constant (about 23 to about 31 ns), has a slightly shorter attenuation length, a very fast light output (initial photons), and the energy resolution of LuI$_3$:Ce coupled to a PMT and measured at 662 keV was about 10% (FWHM). Timing resolution of a LuI$_3$-PMT operating in coincidence mode was measured to be about 210 ps (FWHM) to about 195 ps (FWHM).

LuI$_3$ has a hexagonal crystal structure, a density of 5.6 g/cm$^3$, and can be grown directly from the melt by techniques such as Bridgman and Czochralski. This is a useful property because these melt-based techniques are generally easier to scale-up and are used in commercial production of scintillators. Crystals have been usefully grown using these methods although other methods for their growth are well known to the skilled artisan. LuI$_3$ is moisture-sensitive and therefore should be hermetically packaged to prevent exposure to moisture.

As will be understood by one of skill in the art, fast scintillators are used in conjunction with methods to calibrate each detector to correct for differential time lags that confuse relative timing measurements. In particular embodiments, such corrections are performed by introducing hardwired delays of appropriate lengths or by software processing based on pre-stored delay times for each detector. Within the practice of the present invention scintillators are used in individual detectors (detector modules) or read by position-sensitive photodetectors or arrays of photodetectors that detect the light from the scintillation of the crystal or ceramic.

The applications of these fast detectors are not limited to PET cameras. They are also useful in applications where fast decay of the light signal is desirable. One such application is X-ray computed tomography (CT), where, as rotation times and individual detector size decreases, detector response time become more important. The high linearity of output of the scintillators of the present invention is of particular use in this application.

Notable parameters for the scintillation crystals used in spectroscopy of energetic photons (gamma-rays) as well as neutrons at room temperature applications include high light output, high stopping efficiency, fast response, low cost, good linearity, and minimal afterglow.

EXAMPLE 1

LuI$_3$ Crystals, Bridgman Method

In making crystals, ultra-dry forms of LuI$_3$ and CeI$_3$ were used with 99.99% purity. A two zone Bridgman furnace was used with temperature in the hotter zone above the melting point LuI$_3$ (1050° C.) and that of the cooler zone below the melting point. The amount of CeI$_3$ in the feed material was adjusted to produce LuI$_3$ samples with varying Ce$^{3+}$ concentration. Most growth runs were performed with 0.5% and 5.0% (on a molar basis) cerium concentration, although runs can also be performed with other Ce$^{3+}$ concentrations (e.g., 0.1%, 10%, 20%, 30%, 40%, 50%, 60%, and up to or less than 100%). LuI$_3$ crystals as large as ~1 cm$^3$ were grown using this process. These crystals were cut from the solid ingots to produce small samples ($\leq 0.3$ cm$^3$ size) for measurements.

Scintillation properties of the LuI$_3$ crystals were then measured. For some measurements, packaged samples were used because LuI$_3$:Ce crystals were sensitive to moisture. This involved placing a LuI$_3$:Ce crystal inside a metal can on a quartz window. The crystal was attached to the quartz with a clear optical epoxy (e.g., EPO-TEK #301-2) The space around the crystal in the can was filled with SiO$_2$ powder. The top of the can was finally sealed by attaching a metal disc using epoxy.

EXAMPLE 2

LuI:Ce, Scintillation Properties

Characterization of the scintillation properties of LuI$_3$ crystals grown by the Bridgman process involved measurement of the light output, the emission spectrum, and the fluorescent decay time of the crystals. Energy and timing resolution of the LuI$_3$:Ce crystals and their proportionality were also measured. Based on its high atomic number constituents and high density, Lu$_{1-x}$I$_3$Ce$_x$ showed high gamma-ray stopping efficiency. The attenuation length of 511 keV photons in LuI$_3$:Ce was 1.7 cm.

Emission Spectrum

The emission spectrum of the LuI$_3$:Ce scintillators was measured. The LuI$_3$:Ce samples were excited with radiation from a Philips X-ray tube having a copper target, with power settings of 35 kVp and 15 mA. The scintillation light was passed through a McPherson monochromator and detected by a Hamamatsu R2059 photomultiplier tube with a quartz window.

Figure 4:
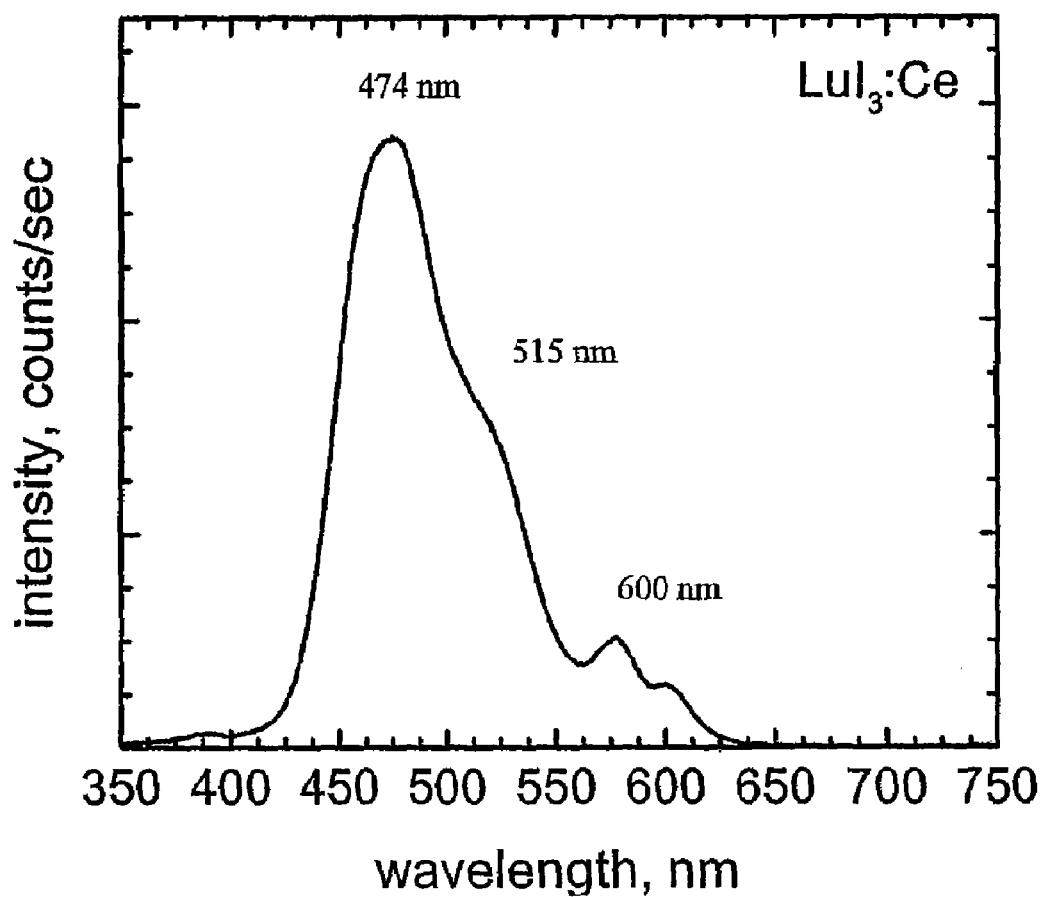
FIG. 4 plots a radioluminescence spectrum of a $LuI_3$:Ce (0.5% Ce concentration) scintillator. The main emissions at 474 and 515 nm are due to $Ce^{3+}$ luminescence.

FIG. 4 shows the normalized emission spectra for LuI$_3$:Ce samples with a 0.5% Ce concentration. As seen in FIG. 4, the peak emission wavelength for the LuI$_3$:Ce sample is at about 474 nm. The smaller peaks observed in the 550-620 nm region may be due to impurities that may be present in the Sample. Emission spectrum measured for LuI$_3$:Ce with 5.0% Ce was very similar to that displayed in FIG. 4. The peak emission wavelength of 474 nm for LuI$_3$:Ce matches well with the spectral response of the photomultiplier tubes as well as silicon photodiodes that are used in scintillation detection. The emission spectrum for LuI$_3$:Ce with 5.0% Ce$^{3+}$ is similar to that shown in FIG. 4.

Decay Time

Figure 5:
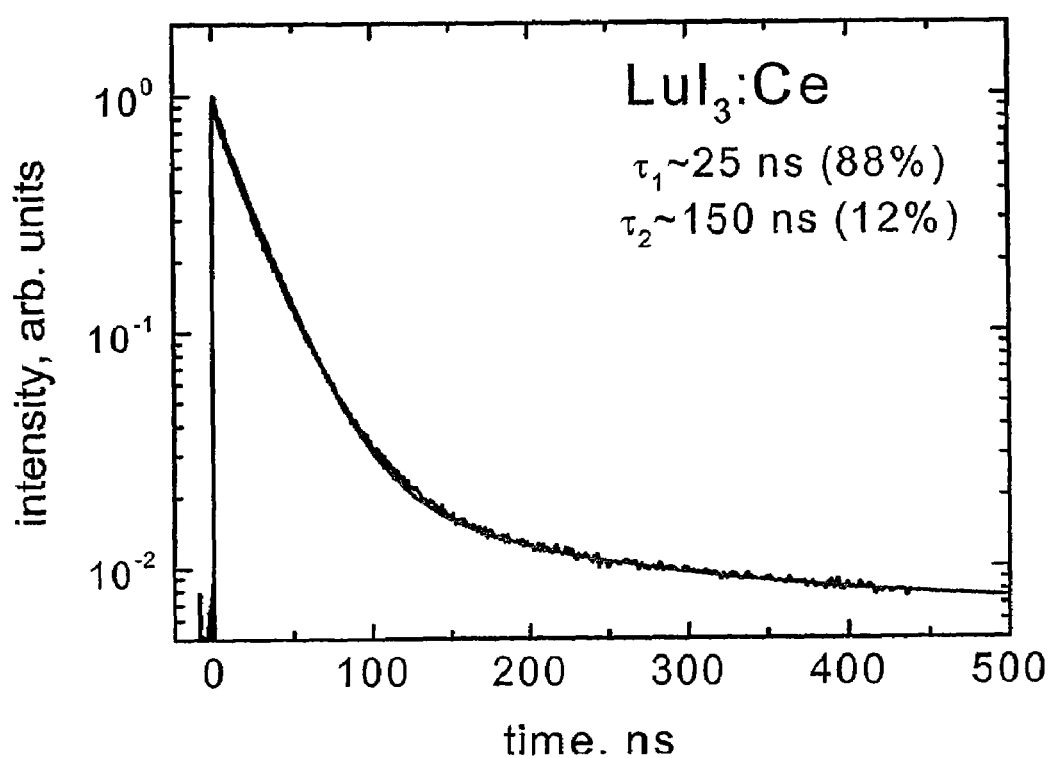
FIG. 5 provides a time profile of $LuI_3$:Ce (5% Ce concentration) scintillation.

The fluorescent decay time profile of a LuI$_3$:Ce scintillation has been measured using the delayed coincidence method as described in Bollinger and Thomas (*Rev. Sci. Instr.*, 32:1044 (1961), the teachings of which are incorporated herein by reference) by exposing the crystal to 662 keV gamma-rays ($^{137}$Cs source). FIG. 5 shows the time profile recorded for a LuI$_3$:Ce (5.0% Ce concentration) sample along with a multi-exponential fit to the data. The principal decay constant for the sample is about 25 ns (most likely arising from direct electron-hole capture on Ce$^{3+}$ site) and this component covers about 88% of the integrated light output. A longer decay component with 150 ns time constant is also present in the LuI$_3$:Ce sample with 5.0% Ce doping and covers about 12% of the integrated light emission. For LuI$_3$ with 0.5% Ce doping, the principal decay constant is about 31 ns, which covers >80% of the integrated light output, with the remaining light emitted via a 230 ns decay component. Virtually no rise time is observed for the LuI$_3$ sample with 5.0% Ce$^{3+}$. A rise time of ~4 ns was observed for the LuI$_3$ sample with 0.5% Ce$^{3+}$. From this, Applicants believe that a higher concentration of Ce will improve the timing properties of the LuI$_3$:Ce crystals.

Light Output and Energy Resolution

Figure 6:
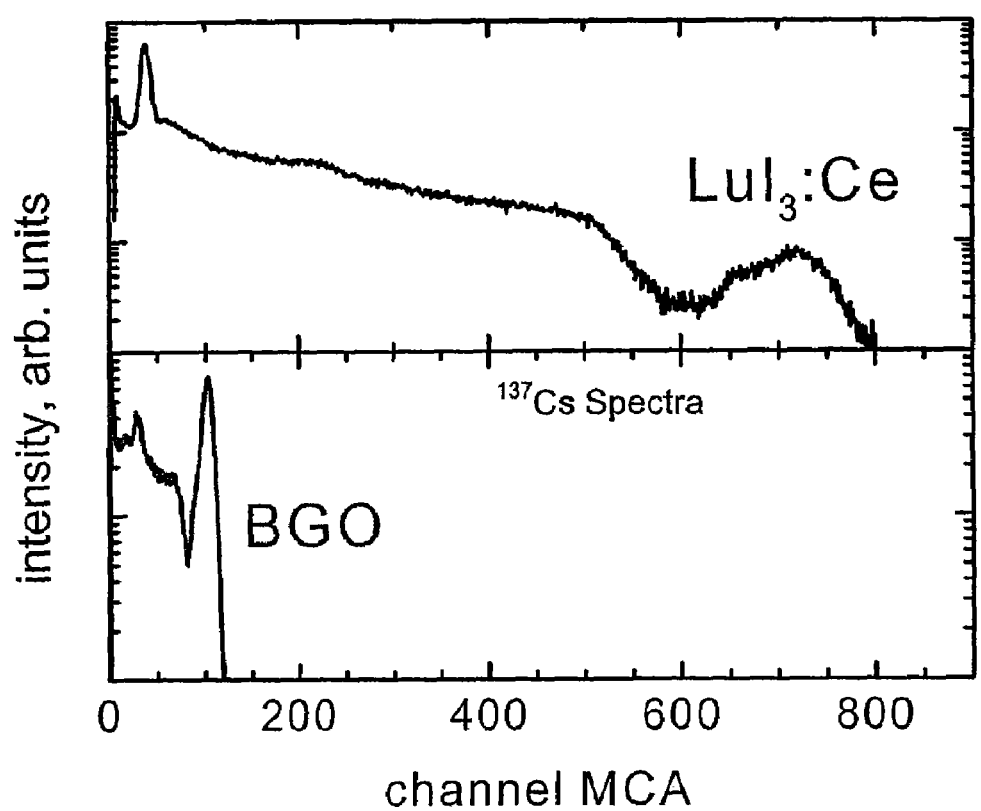
FIG. 6 presents the $^{137}Cs$ spectra recorded with $LuI_3$:Ce and BGO scintillators coupled to a PMT under substantially identical operating conditions.

The light output (or luminosity) of LuI$_3$:Ce crystals was measured with samples (doped with 0.5% and 5.0% Ce$^{3+}$ concentration) by comparing their response and the response of a calibrated BGO scintillator (with 7500 photons/MeV light output) to the same isotope (662 keV γ-rays, $^{137}$Cs source, see FIG. 6). These measurements involved optical coupling of a LuI$_3$:Ce sample to a photomultiplier tube, irradiating the scintillator with 662 keV photons and recording the resulting pulse height spectrum using standard NIM electronics. In order to maximize light collection, LuI$_3$:Ce crystals were wrapped in reflective, white Teflon tape on all faces (except the one coupled to a photomultiplier (PMT)). FIG. 6 shows the pulse height spectra for both LaBr$_3$:Ce and BGO under $^{137}$Cs irradiation and amplifier shaping time of 4.0 microseconds. This shaping time was long enough to allow full light collection from both the scintillators. The photomultiplier (PMT) bias and amplifier gain were the same for both spectra. Based on the recorded photopeak positions for LuI$_3$:Ce and BGO, and by taking into account the photocathode quantum efficiency for BGO and LuI$_3$:Ce, the light output of LaBr3:Ce crystal with 5.0% Ce concentration was found to be about 50,000 photons/MeV at room temperature, which is about 7 times higher than that of BGO (and about 2 times higher than that of LSO). The light output measured for a 0.5% Ce sample was similar to that measured for the 5.0% Ce sample. The measured light output of LuI$_3$:Ce is about 30% higher compared to that of NaI(Tl). Based on the light output and the decay time measurements the initial photon intensity, a figure of merit in timing applications, was estimated to be 1800 photon/(ns×MeV) for LuI$_3$:Ce (5.0% Ce concentration), which is almost 10 times higher than that for NaI(Tl).

Gamma-Ray Spectroscopy

Figure 7:
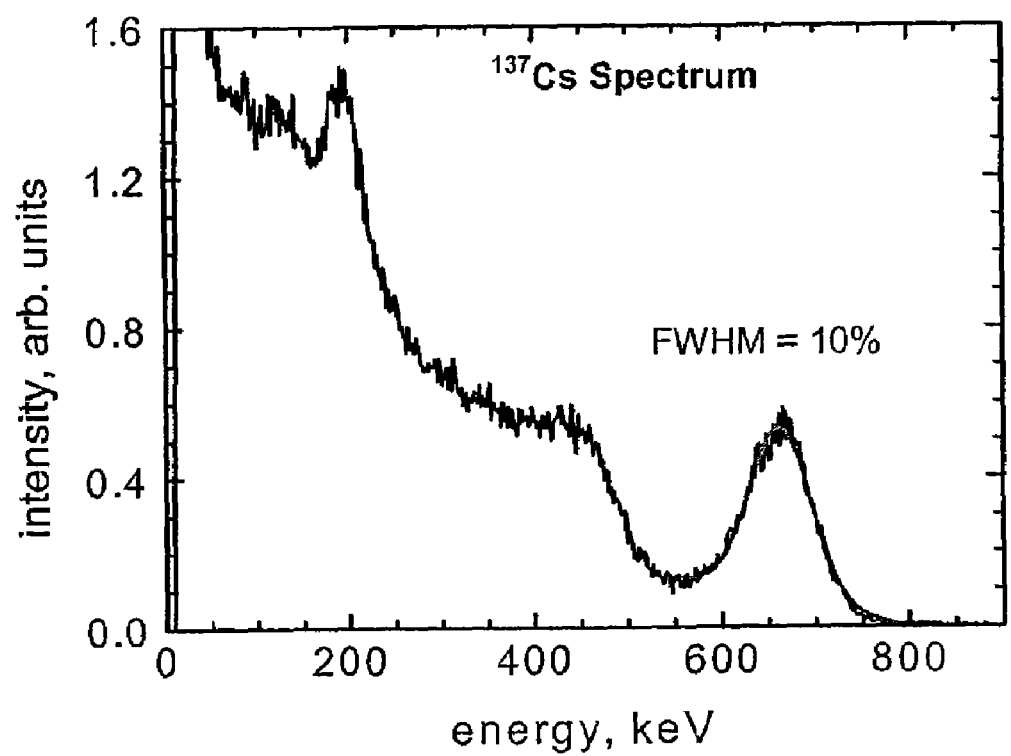
FIG. 7 plots the $^{137}Cs$ spectrum collected with a 0.3 $cm^3$ $LuI_3$:Ce (5% Ce concentration) crystal coupled to a PMT. The energy resolution of 662 keV photopeak is approximately 10% (FWHM) at room temperature.

Gamma-ray spectroscopy was conducted using a LuI$_3$:Ce scintillator coupled to a PMT. The scintillator was covered with Teflon tape and irradiated with 662 keV gamma-rays ($^{137}$Cs source). The PMT signal was processed with a spectroscopy amplifier (Canberra Model 2022) and a gamma-ray spectrum was collected using a multi-channel analyzer residing in a personal computer. FIG. 7 shows a $^{137}$Cs spectrum collected in this manner and the energy resolution of the 662 keV peak was measured to be about 10% (FWHM) at room temperature. The energy resolution was mostly limited by the optical quality of the LuI$_3$:Ce crystals available at present and significant improvement is expected as the crystal growth of LuI$_3$:Ce is optimized and larger, higher quality crystals are produced. The low energy shoulder on the 662 keV photopeak has been attributed to escape of Lu K-edge X-rays.

Proportionality of Response

Figure 8:
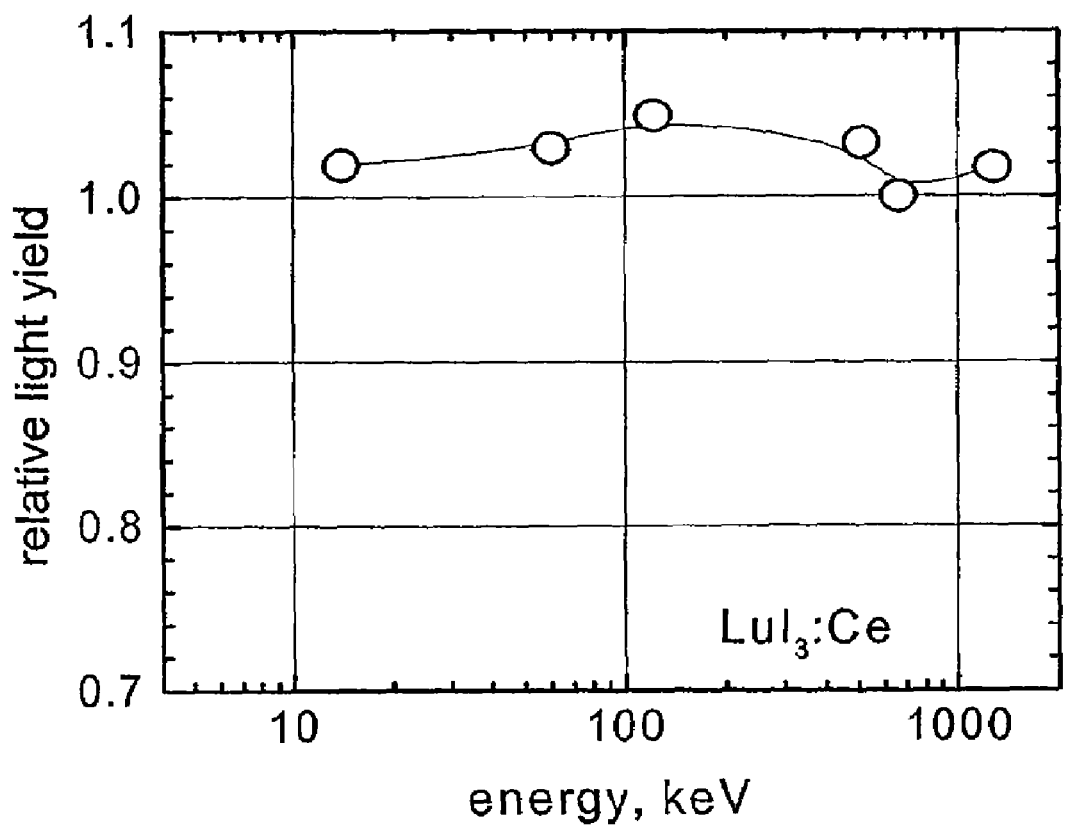
FIG. 8 plots the proportionality of response as a function of gamma-ray energy for a $LuI_3$:Ce (0.5% Ce concentration) scintillator.

Proportionality of response (or linearity) of LuI$_3$:Ce scintillators was also evaluated. Non-proportionality (as a function of energy) in light yield can be one of the important reasons for degradation in energy resolution of established scintillators such as NaI(Tl) and CsI(Tl) (Dorenbos et al., *IEEE Trans. Nucl. Sci.* 42:2190-2202 (1995); Moses, *Nucl. Inst. Meth. A* 487:123-128 (2002)). Light output of LuI$_3$:Ce was measured under excitation from isotopes such as $^{241}$Am (60 keV γ-rays), $^{57}$Co (14 keV X-rays and 122 keV γ-rays), and $^{137}$Cs (662 keV γ-rays). A LuI$_3$:Ce crystal (0.5% Ce concentration) was wrapped in Teflon tape and coupled to a PMT. Pulse height measurements were performed using standard NIM equipment with the scintillator exposed to different isotopes. The same settings were used for PMT and pulse processing electronics for each isotope. From the measured peak position and the known γ-ray energy for each isotope, the light output (in photons/MeV) at each γ-ray energy was estimated. The data points were then normalized with respect to the light output value at 662 keV energy and the results (shown in FIG. 8) indicate that LuI$_3$:Ce is a fairly proportional scintillator. Over the measured energy range, the non-proportionality in light yield was about 5% for LuI$_3$:Ce, which is better than that for many established scintillators. For example, over the same energy range, the non-proportionality is about 35% for LSO:Ce and about 20% for NaI(Tl) and CsI(Tl) has been reported (Gillot-Noel et al., *IEEE Trans. Nucl. Sci.* 46:1274-1284 (1999)).

Coincidence Timing Resolution

Coincidence timing resolution of LuI$_3$:Ce crystals was measured. This involved irradiating a BaF$_2$ and a LuI$_3$:Ce (0.5% Ce concentration) scintillator, each coupled to a fast PMT (Hamamatsu R-5320, operated at −2000V) with 511 keV positron annihilation γ-ray pairs (emitted by a 68Ga source). The BaF$_2$-PMT detector formed a "start" channel in the timing circuit, while the LuI$_3$-PMT detector formed the "stop" channel. The signal from each detector was processed using two channels of a Tennelec TC-454 CFD that had been modified for use with fast (sub-ns) rise-time PMTs. The time difference between the start and stop signals was digitized with a Tennelec TC-862 TAC and a 16-bit ADC, resulting in a TDC with 7.5 ps per bin resolution. Data were accumulated until the coincidence timing distribution had more than 10,000 counts in the maximum bin. FIG. 9 shows the coincidence timing resolution plot acquired in this manner with a LuI$_3$:Ce crystal having 0.5% Ce$^{3+}$ concentration. The timing resolution for this crystal was measured to be about 210 ps (FWHM). The timing resolution for two BaF$_2$ detectors in coincidence with each other was measured to be 210 ps (FWHM) in this study.

Basic PET Configuration

Figure 10:
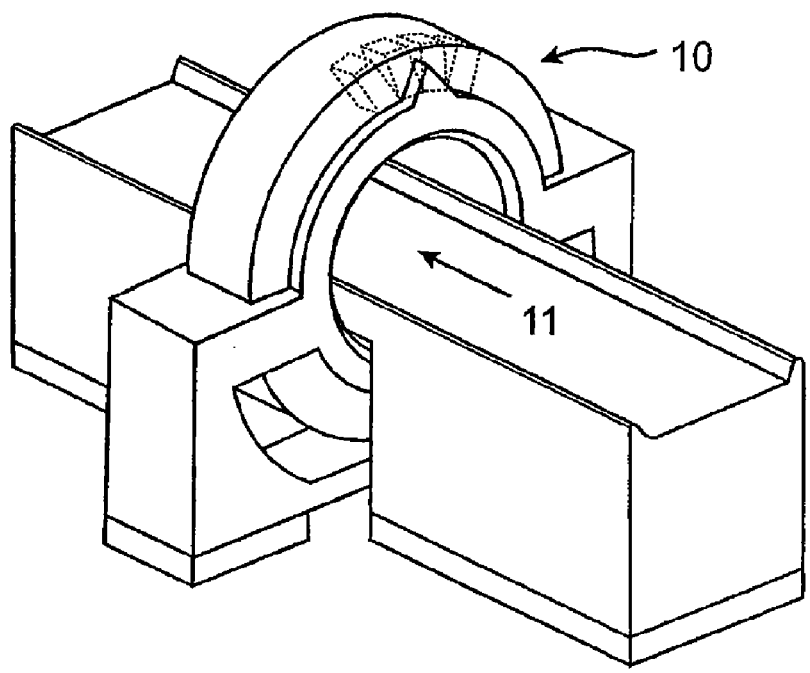
FIG. 10 shows a schematic of a positron emission scanner system.

A PET camera system typically comprises of a polygonal or circular ring of radiation detectors (10) placed around a patient area (11), as shown in FIG. 10. In some embodiments radiation detection begins by injecting or otherwise administering isotopes with short half-lives into a patient's body placeable within the patient area (11). As noted above, the isotopes are taken up by target areas within the body, the isotope emitting positrons that are detected when they generate paired coincident gamma-rays. The annihilation gamma-rays move in opposite directions, leave the body and strike the ring of radiation detectors (10).

Figure 11:
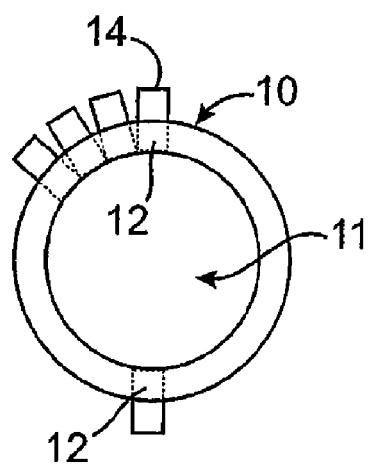
FIG. 11 shows a schematic of the detector arrangement for a positron emission scanner system.

As shown in FIG. 11, the ring of detectors (10) includes an inner ring of scintillators (12) and an attached ring of light detectors or photomultiplier tubes (14). The scintillators (12) respond to the incidence of gamma rays by emitting a flash of light (scintillation) that is then converted into electronic signals by a corresponding adjacent photomultiplier tube or light detectors (14). A computer control system (not shown) records the location of each flash and then plots the source of radiation within the patient's body. The data arising from this process is usefully translated into a PET scan image such as on a PET camera monitor by means known to those in the art.

Figure 12:
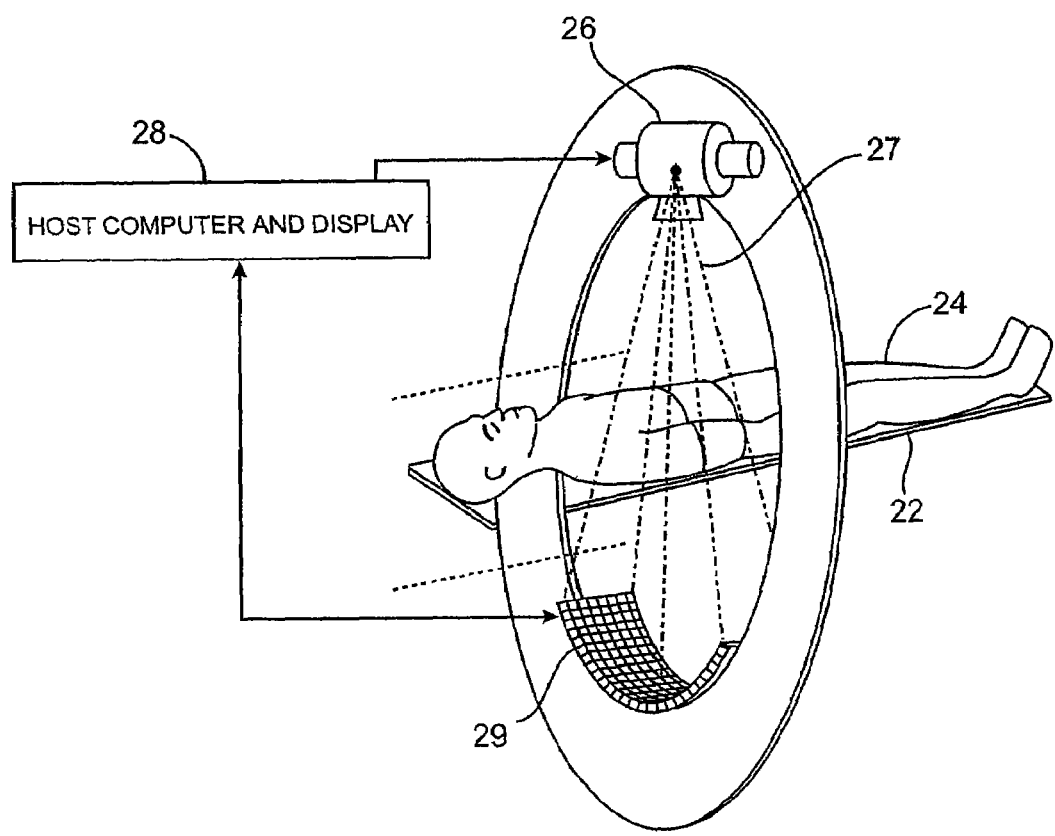
FIG. 12 shows a schematic of an x-ray computed tomography scanner system encompassed by the present invention.

This invention has been discussed in terms of LuI$_3$:Ce crystal scintillators for use in PET, and particularly useful in time-of-flight PET. Such application of the technology is illustrative only. Many, indeed most, ionizing radiation applications will benefit from the inventions disclosed herein. Specific mention is made to X-ray CT, X-ray fluoroscopy, X-ray cameras (such as for security uses), and the like. A CT scanner as shown in FIG. 12, as well known to the skilled artisan, typically comprises a patient bed 22, a penetrating X-ray source 26 (i.e., an X-ray tube), a detector assembly 29 and associated processing electronics 29, and a computer and software for image reconstruction, display, manipulation, post-acquisition calculations, storage and retrieval 28.

EXAMPLE 3

This example describes further preparation of crystals of LuI$_3$:Ce and evaluation of their scintillation properties. Similar to the description above, LuI$_3$:Ce crystals were prepared using the Bridgman method with varying Ce$^{3+}$ concentrations. Light output, emission spectra, decay time spectra and proportionality studies were conducted using these crystals. However, properties such as light output of LuI$_3$:Ce samples described in Example 3 were higher than that for crystals that were investigated and described above, which was possibly due to improved quality of the crystals selected for evaluation and herein described in Example 3.

Production of Crystals

As described above, the Bridgman method was used in making crystals (see, e.g., Example 1). Both the vertical and horizontal orientations of the Bridgman method can be used in producing crystals. The vertical Bridgman method is more commonly used in scintillator crystal production, although the horizontal approach differs in several aspects including, for example, production of a sharper definition of the critical liquid/solid interface; less stress on the crystal during solidification and cooling; and simple implementation of a zone leveling process to achieve uniform dopant concentration across the length of the ingot. While the vertical Bridgman method was primarily used in producing crystals according to Examples 1 and 2, the horizontal orientation of the Bridgman method was also used in producing crystals examined and discussed below.

Prior to actual Bridgman growth, LuI$_3$ doped with an appropriate amount of Ce$^{3+}$ was prepared. A wide range of Ce$^{3+}$ concentration (0.5% to 20%) was evaluated, although additional concentrations can also be utilized. Ultra-dry, high purity LuI$_3$ was used and Ce$^{3+}$ was incorporated in a range of about 0.5% to 20% (on molar weight basis) by adding CeI$_3$ to the mixture. These constituents were mixed and then placed in an ampoule (e.g., quartz, tantalum, or glassy carbon crucibles). The ampoule was evacuated, sealed and then heated in a single zone furnace to a temperature above the melting point of LuI$_3$ and CeI$_3$ (e.g., about 1100° C.), thus allowing the constituents to mix and react in the melt phase to form LuI$_3$:Ce. Upon cooling, the solid phase of LuI$_3$:Ce was available for use as feed material for the Bridgman growth process. A two zone Bridgman furnace, as described above, was used for LuI$_3$:Ce growth. In use, the higher temperature zone ($T_1$) of the furnace was kept above the melting point of the compound, and the lower temperature zone ($T_2$) was maintained below the melting point. Thus, feed material in the furnace first melts while in the zone defined by $T_1$ and then crystallizes out in the zone defined by $T_2$.

The speed at which the solid-liquid interface is moved, as determined by the temperature gradient in the furnace, and the shape of the interface are parameters influential in growing high quality crystals. In one embodiment, the temperature $T_1$ was set at 1100° C., while the temperature $T_2$ was 900° C. Growth rate (e.g., the rate of motion of zone $T_1$) effects how close the conditions at the solid-liquid interface come to equilibrium and, at very slow rates, the system operates close to equilibrium. Typical growth rates for the Bridgman process are about 1-10 mm/hour, though a growth rate of about 30 mm/day was used to produce crystals described herein. Growth rates ranging from about 1 mm/day to about 1 cm/hour may be utilized. Additionally, in some instances zone leveling of the ingot was performed in order to maintain a uniform Ce$^{3+}$ doping level over its entire length.

Physical Properties of LuI$_3$:Ce Crystals

Characterization of the physical properties of high quality LuI$_3$:Ce crystals included X-ray diffraction analysis and optical transmission measurements.

X-ray diffraction analysis of the LuI$_3$:Ce crystals was conducted using a Rigaku X-Ray diffractometer (Rotaflex RTP-500 with copper K-alpha radiation). In view of the hygroscopic nature of the LuI$_3$ crystals, the sample was placed in a helium chamber and then positioned on the table of the diffraction apparatus. The X-ray diffraction pattern for the grown LuI$_3$:Ce crystal confirmed that the sample was a single crystal with a hexagonal structure (data not shown). The most intense peak for the sample occurred at the two theta value of 52.8°.

Optical spectroscopy of the LuI$_3$:Ce crystals was also performed. The optical absorption edge was determined to be about 255 nm, which indicated that the bandgap of LuI$_3$ was about 4.6 eV. Using a McPherson monochromator, optical transmission measurements were also performed in the range of about 400 to about 600 nm, over which LuI$_3$:Ce emits light. A calibrated silicon photodiode was used and the optical response of the photodiode was measured with and without the LuI$_3$:Ce crystal placed on it as a function of the incident wavelength. The optical transmission for the sample (estimated from the ratio of the photodiode response with and without LuI$_3$:Ce) was found to be greater than 80% in the 400-600 nm range in samples measured.

Light Output Measurements

The light output of LuI$_3$:Ce crystals was measured with samples doped with 0.5%, 5.0%, 10.0%, and 20.0% Ce$^{3+}$ concentrations in substantially the same manner as the light output and energy resolution measurement described above (see, e.g., Example 2).

Figure 13:
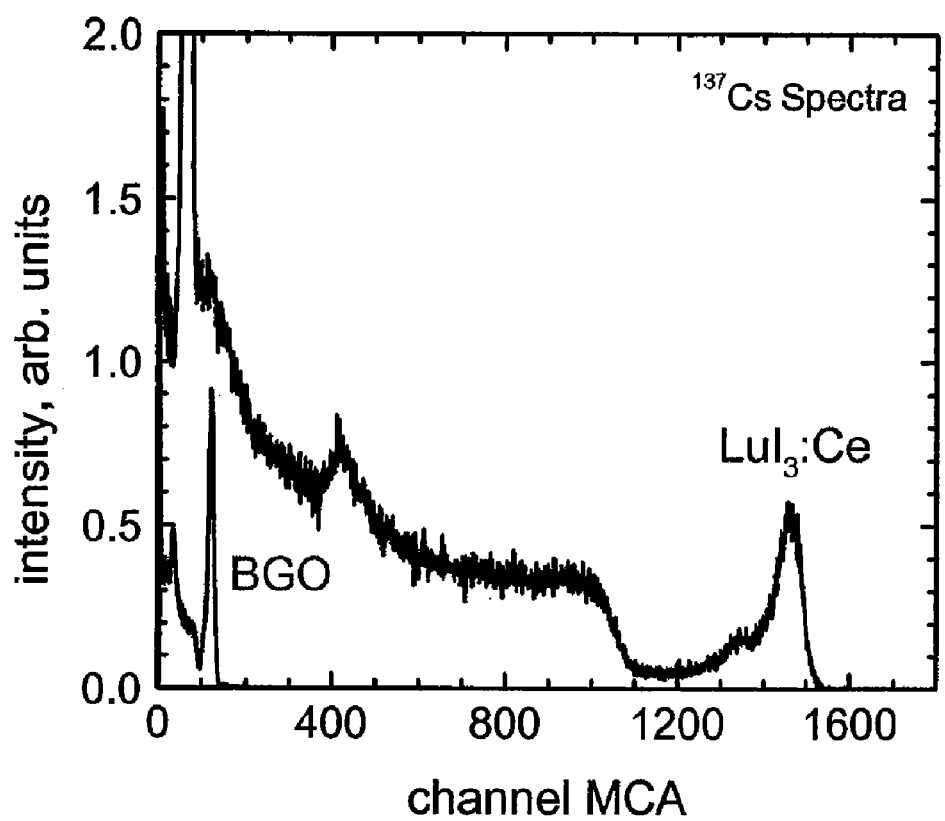
FIG. 13 plots the $^{137}Cs$ spectra recorded with $LuI_3$:Ce (5.0% $Ce^{3+}$ concentration) and BGO scintillators coupled to a PMT under substantially identical operating conditions.

Comparison of the photopeak position obtained with various LuI$_3$:Ce crystals for 662 keV photon energy to that with BGO provided an estimation of light output for LuI$_3$:Ce crystals with different Ce$^{3+}$ concentrations. Pulse height spectra for a LuI$_3$:Ce crystal (with 5.0 % Ce concentration) and a BGO crystal under $^{137}$Cs irradiation and amplifier shaping time of 4.0 microseconds are shown in FIG. 13. The shaping time observed was sufficient to allow full light collection from both the scintillators. Based on the recorded photopeak positions for LuI$_3$:Ce and BGO as illustrated in FIG. 13, and by taking into account the photocathode quantum efficiency for BGO and LuI$_3$:Ce emissions, light output of LuI$_3$:Ce crystal with 5% Ce was estimated at about 100,000 photons/MeV. This is the highest recorded light yield for an inorganic scintillator and is about 4 times the value for LSO, about 12 times the value for BGO and about 2.6 times the value for NaI:Tl. The energy resolution of the 662 keV photopeak recorded with LuI$_3$:Ce crystal (0.5% Ce) was about 3.5% (FWHM). Thus, improvement of the crystal quality of LuI$_3$:Ce samples by altering the production method led to a considerable improvement in the light output properties of the samples.

The theoretical maximum light output ($L_{max}$) of ionic crystals such as LuI$_3$ can be expressed as: $L_{max}=10^6/(\beta \cdot E_g)$ photons/MeV; where $\beta$ is a numerical coefficient with values between about 1.5 and about 2.5 for ionic crystals, and $E_g$ is the bandgap of the scintillator. Based on this expression and the measured bandgap of about 4.6 eV for LuI$_3$, the theoretical maximum light output for LuI$_3$ can be as high as 145,000 photons/MeV. Thus, further improvement in light output of LuI$_3$:Ce crystals could be possible upon further refinement of crystal production and quality. The light output results for LuI$_3$:Ce crystals with different Ce$^{3+}$ concentrations are summarized in Table III and our data indicate that Ce$^{3+}$ concentrations of about 0.5% and about 5% provide high light output (about 100,000 photons/MeV).

Emission Spectrum

Figure 14:
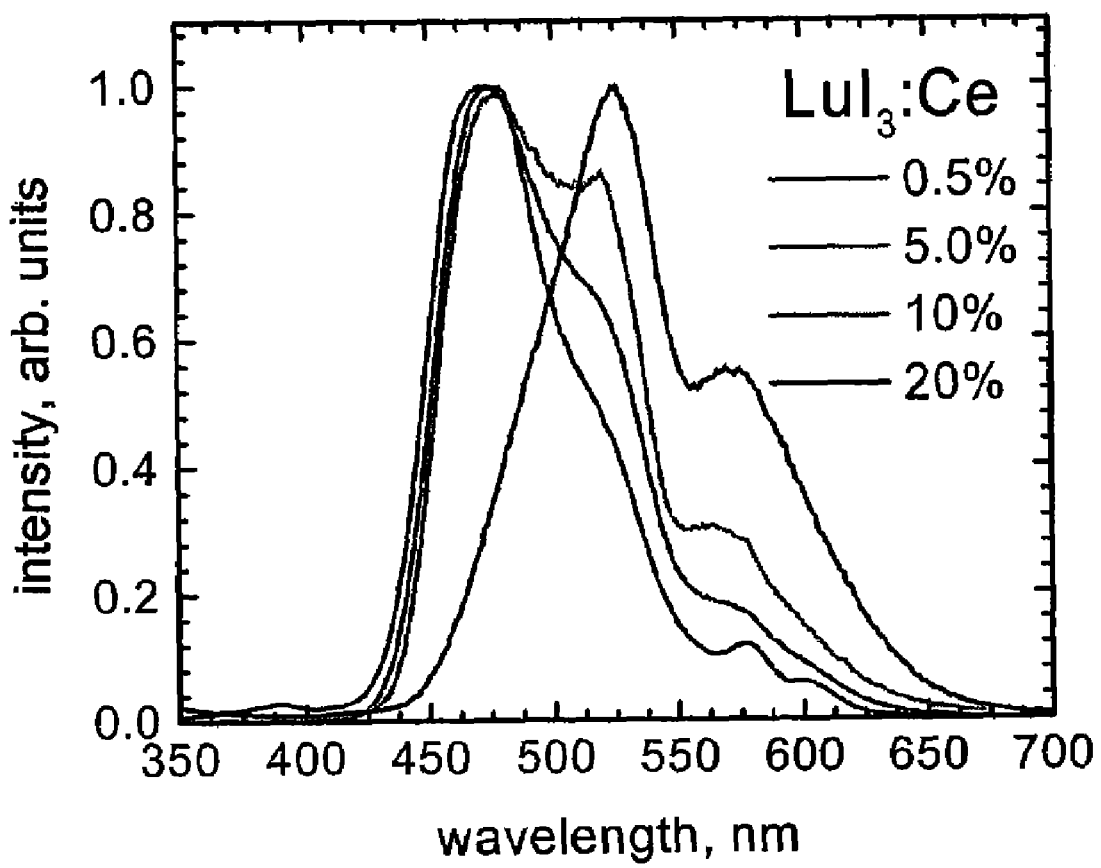
FIG. 14 plots a radioluminescence spectra of $LuI_3$:Ce crystals with 0.5%, 5.0%, 10% and 20% $Ce^{3+}$ concentrations.

The emission spectra of the LuI$_3$:Ce scintillators with samples doped with 0.5%, 5.0%, 10.0%, and 20.0% Ce$^{3+}$ concentrations was measured as described above (see, e.g., Example 2). FIG. 14 illustrates the normalized emission spectra for LuI$_3$:Ce samples doped with 0.5%, 5.0%, 10.0%, and 20.0% Ce$^{3+}$ concentrations. As seen in FIG. 14, emission peaks with $\lambda_{max}$ of about 470 and 525 nm (characteristic for Ce$^{3+}$ luminescence due to its 5d→4f transition) were present for Ce$^{3+}$ concentrations of 0.5%, 5.0%, and 10.0%. For the LuI$_3$ sample with 20% Ce$^{3+}$, emission peaks with $\lambda_{max}$ of 525 and 575 nm were observed.

Decay Time

Figure 15:
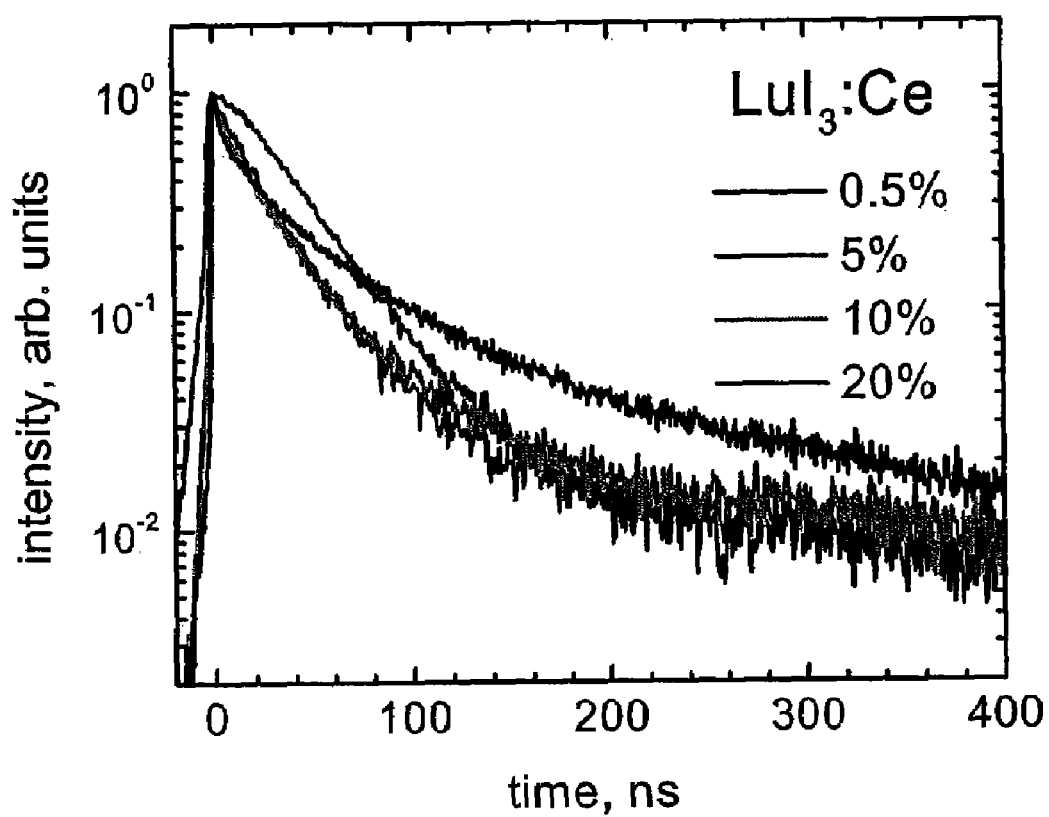
FIG. 15 provides a profile of decay time spectra for $LuI_3$ crystals with 0.5%, 5.0%, 10% and 20% $Ce^{3+}$ concentrations. The rise and decay time(s) for these timing plots, based on multi-exponential fits to the data are listed in Table III.

The fluorescent decay times of LuI$_3$:Ce samples doped with 0.5%,5.0%, 10.0%, and 20.0% Ce$^{3+}$ concentrations were measured using the delayed coincidence method as described above (see, e.g., Example 2). The results are presented in FIG. 15.

The decay time spectrum for LuI$_3$:Ce samples with varying Ce$^{3+}$ concentration was measured after x-ray exposure (see FIG. 15) and was fitted to the sum of exponentials (rise and multiple decay times) and a time-independent background. The fit results are also shown in Table III. As seen in Table III, all samples show a very fast principal decay constant (<40 ns). It has been noted that as the Ce$^{3+}$ concentration increases beyond 0.5%, the risetime improves significantly. This is an important consideration for PET imaging because the risetime of a scintillator plays an important role in its timing resolution. The actual risetime of LuI$_3$:Ce samples with higher Ce$^{3+}$ concentrations may be even faster since the measured values may be mostly due to light reflecting in the crystal.

TABLE III

Scintillation Properties of LuI$_3$:Ce with Different Ce Concentrations

| Ce % | Light Yield photons/MeV | Emission nm | Risetime ns | Decay time(s) ns |
| --- | --- | --- | --- | --- |
| 0.5 | 95,000 | 474 | ~5 | 31 (88%), 230 (12%) |
| 5 | 100,000 | 475 | <1 | 23 (74%), 105 (26%) |
| 10 | 70,000 | 477 | <1 | 24 (75%), 180 (25%) |
| 20 | 38,000 | 525 | <1 | 4 (4%), 39 (49%), 210 (47%) |

From the properties listed in Table III, high energy and timing resolution can be expected for the LuI$_3$ samples (e.g., samples with 0.5% Ce$^{3+}$ concentrations), both of which are important for PET imaging.

Energy Resolution Measurements

Figure 16:
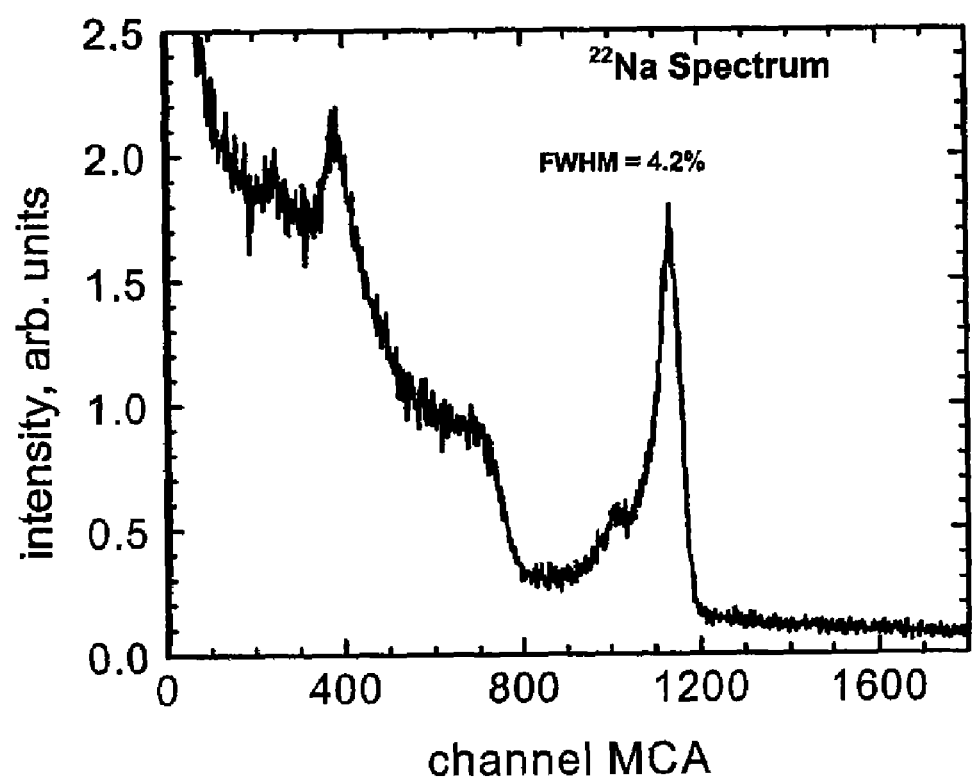
FIG. 16 plots the $^{22}Na$ gamma-ray spectrum recorded with a $LuI_3$:Ce (5.0% $Ce^{3+}$ concentration; $\leq 1$ $cm^3$ size) crystal coupled to a PMT. The energy resolution of 511 keV peak is about 4.2% (FWHM) at room temperature.

The gamma-ray energy resolution of LuI$_3$:Ce scintillators was measured by coupling unpackaged LuI$_3$:Ce scintillators (e.g., 5.0% Ce, $\leq 1$ cm$^3$ size) to a photomultiplier tube with a bialkali photocathode and a quartz window. The scintillators were coated with Teflon tape to maximize light collection and irradiated with 511 keV gamma-rays ($^{22}$Na source). The resulting PMT signal was processed with a preamplifier (Canberra #2005) and then shaped with a spectroscopy amplifier (Canberra #2022). A $^{22}$Na pulse height spectrum was recorded at shaping time of 4 μs, as shown in FIG. 16. Energy resolution for the 511 keV peak was computed to be about 4% (FVHM) at room temperature. This energy resolution was much better than that recorded with conventional PET scintillators such as LSO, GSO and BGO which provide energy resolution of ~10% (FWHM) at 511 keV, even for small crystals.

Proportionality of Response

Similar to that described above, proportionality of response (or linearity) of the LuI$_3$ crystal scintillators was evaluated. Light output of LuI3:Ce crystal was measured under excitation from isotopes such as $^{241}$Am (60 keV γ-rays), $^{57}$Co (14 and 122 keV γ-rays), $^{22}$Na (511 keV and 1275 keV γ-rays) and $^{137}$Cs (662 keV γ-rays). A LuI$_3$:Ce crystal (5.0% Ce concentration) was wrapped in Teflon tape and coupled to a PMT. Pulse height measurements were performed using standard NIM equipment with the scintillator exposed to different isotopes. The same settings were used for PMT and pulse processing electronics for each isotope. From the measured peak position and the known γ-ray energy for each isotope, the light output (in photons/MeV) at each γ-ray energy was estimated. The data points were then normalized with respect to the light output value at 662 keV energy and results (not shown) indicate that LuI$_3$:Ce is a proportional scintillator. Over the measured energy range of 20 to 1275 keV, the non-proportionality in light yield is ±2.5% for LuI$_3$:Ce which is substantially better than that for many established scintillators. For example, over the same energy range, the non-proportionality is about ±17.5% for LSO and about ±10% for NaI(Tl) and CsI(Tl) (Gillot-Noel et al., *IEEE Trans. Nucl. Sci.* 46:1274-1284 (1999)). The higher proportionality of LuI$_3$:Ce in combination with its high light yield indicates that LuI$_3$:Ce should be able to provide energy resolution superior to that obtained for established scintillators. Thus, the energy resolution of LuI$_3$:Ce crystals capable of being produced by the methods described herein could surpass that of all scintillation materials.

Coincidence Timing Resolution

Coincidence timing resolution of LuI$_3$:Ce crystals with various Ce$^{3+}$ concentrations was measured as described above (see, e.g., Example 2).

Figure 17:
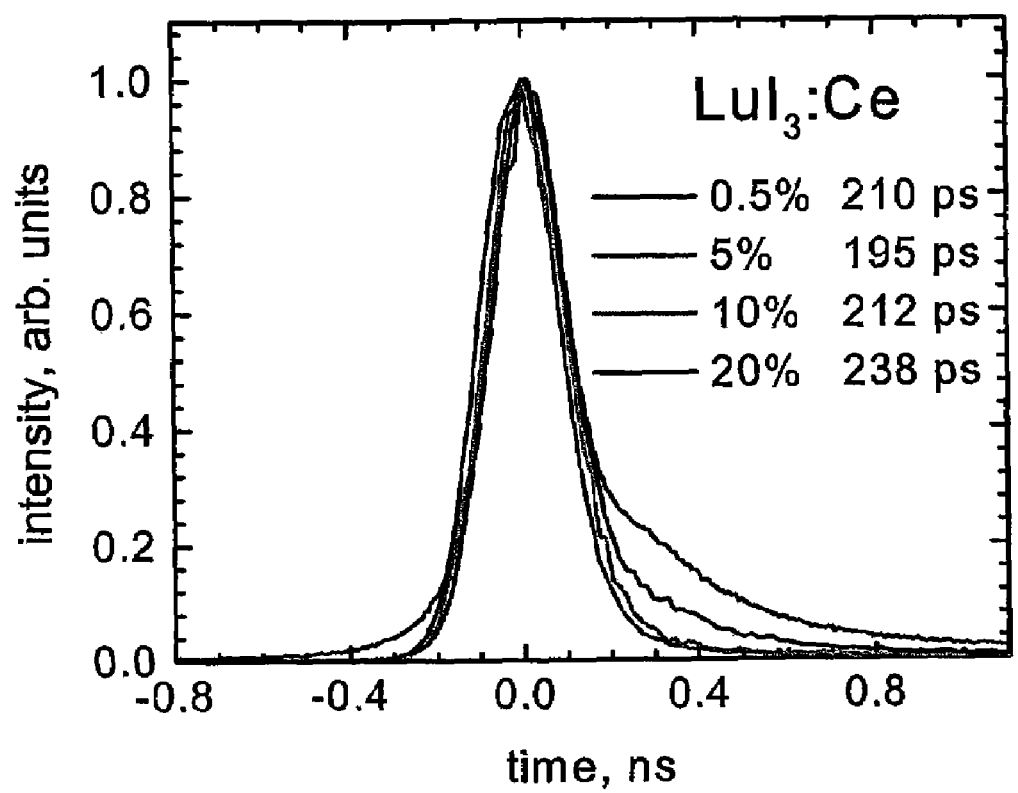
FIG. 17 provides the coincidence timing resolution plots for $BaF_2$ and $LuI_3$ crystals with 0.5%, 5.0%, 10% and 20% $Ce^{3+}$ concentrations. Also shown in the figure are the timing resolutions (FWHM) for each $Ce^{3+}$ doping level.

FIG. 17 shows coincidence timing resolution plots acquired at room temperature in this manner with LuI$_3$:Ce crystals having 0.5%, 5%, 10%, and 20% Ce$^{3+}$ concentrations that were placed in the "stop" channel of the timing circuit and BaF$_2$ present in the "start" channel, and the coincidence timing resolution was measured to be 210 ps, 195 ps, 212 ps, and 238 ps (FWHM), respectively at room temperature. The results demonstrated that LuI$_3$:Ce scintillators provide excellent timing resolution. For the sample with 5.0% Ce$^{3+}$ concentration, the timing resolution was superior to that for two BaF$_2$ crystals in coincidence (210 ps-FWHM), a benchmark for timing applications. Improved timing performance of LuI$_3$:Ce crystals with 5% Ce$^{3+}$ concentration can be explained on the basis of high light output, and fast rise and decay time constants for this composition (see Table III). These results indicate that LuI$_3$:Ce crystals (e.g., with 5.0% Ce) can be suitable for time-of-flight (TOF) PET in view of their excellent timing resolution.

Although the foregoing invention has been described in some detail by way of illustration and example for purposes of clarity of understanding, it will be obvious that certain changes and modifications may be practiced within the scope of the invention. All publications and patents mentioned in this specification are herein incorporated by reference into the specification to the same extent as if each individual publication or patent was specifically and individually indicated to be incorporated herein by reference.

What is claimed is:

1. A scintillator comprising lutetium iodide and a trivalent cerium dopant.

2. The scintillator of claim 1, wherein said dopant is present from about 0.1% to less than 100% by molar weight.

3. The scintillator of claim 1, wherein said dopant is present in an amount of from about 0.5% to about 5.0% by molar weight.

4. The scintillator of claim 3, wherein said dopant is present in an amount of about 5.0% by molar weight.

5. The scintillator of claim 1, wherein said dopant is present in an amount of from about 0.5% to about 20% by molar weight.

6. The scintillator of claim 5, wherein said dopant is present in an amount of about 10% by molar weight.

7. The scintillator of claim 5, wherein said dopant is present in an amount of about 20% by molar weight.

8. The scintillator of claim 1 having a fast component with a decay constant of about 23 to about 31 nanoseconds and a slow component, if present, with a decay constant of about 120 to about 230 nanoseconds.

9. A positron emission tomography scanner system comprising:
a patient area;
an assembly of radiation detectors disposed adjacent the patient area, wherein the radiation detectors comprise:
a scintillator comprising lutetium iodide and a trivalent cerium dopant;
a scintillation light detector or photomultiplier tube optically coupled to the scintillator; and
electronics coupled to the light detectors or photomultiplier tubes so as to output image data in response to radiation detected by the assembly.

10. The positron emission tomography scanner system of claim 9, wherein said dopant is present from about 0.1% to less than 100% by molar weight.

11. The positron emission tomography scanner system of claim 9, wherein said dopant is present from about 0.5% to about 5.0% by molar weight.

12. The positron emission tomography scanner system of claim 9, wherein said dopant is present at about 5.0% by molar weight.

13. The positron emission tomography scanner system of claim 9, wherein said dopant is present from about 0.5% to about 20% by molar weight.

14. The positron emission tomography scanner system of claim 13, wherein said dopant is present at about 10% by molar weight.

15. The positron emission tomography scanner system of claim 13, wherein said dopant is present at about 20% by molar weight.

16. The positron emission tomography scanner of claim 9, wherein said scintillator is used in coincidence detection positron emission tomography by recording the differential arrival time of two photons so as to localize the annihilation event.

17. The positron emission tomography scanner of claim 16, wherein the localization is to within a distance of less than about 30 cm.

18. The positron emission tomography scanner of claim 9, wherein the radiation detector comprises two or more radiation detectors,
wherein each scintillation light detector comprises a position sensitive detector or array.

19. The positron emission tomography scanner of claim 18, further comprising a means to correct for different timing offsets of each individual radiation detector.

20. The positron emission tomography scanner of claim 19, wherein timing offsets of individual radiation detectors are stored in a memory in the control system.

21. The positron emission tomography scanner of claim 20, wherein for each radiation detector the timing offsets are subtracted from each gamma-ray time arrival value prior to computation of a localization.

22. The positron emission tomography scanner of claim 18, wherein timing signals of individual radiation detectors are equalized by an introduction of individual hardwired delays in signal readout electronics in the control system.

23. An X-ray computed tomography scanner system comprising:
a patient area;
a penetrating X-ray source; and
a detector assembly comprising a scintillator comprising lutetium iodide and a trivalent cerium dopant wherein said dopant is present from about 0.1% to less than 100% by molar weight; and electronics coupled to the detector assembly so as to output image data in response to radiation detected by the assembly.

24. The X-ray computed tomography scanner system of claim 23 wherein said dopant is present from about 0.5% to about 5.0% by molar weight.

25. The positron emission tomography scanner system of claim 24 wherein said dopant is present at about 5.0% by molar weight.

26. The positron emission tomography scanner system of claim 24 wherein said dopant is present at about 0.5% by molar weight.

27. The X-ray computed tomography scanner system of claim 23 wherein said dopant is present from about 0.5% to about 20% by molar weight.

28. The positron emission tomography scanner system of claim 27 wherein said dopant is present at about 10% by molar weight.

29. The positron emission tomography scanner system of claim 27 wherein said dopant is present at about 20% by molar weight.

30. A method of performing time-of-flight positron emission tomography comprising:
administering a patient a detectable label;
positioning the patient within a field of view of a positron emission tomography scanner system, the system comprising a scintillator comprising lutetium iodide ($LuI_3$) and trivalent cerium as a dopant;
detecting positron annihilation emissions from the patient using the positron emission tomography scanner system; and
generating patient image data in response to the detected emissions.

31. The method of claim 30 wherein said scintillator has a timing resolution of less than 500 ps.

32. The method of claim 30, wherein said Cerium dopant is present from about 0.1% to less than 100% by molar weight.

33. The method of claim 32, wherein said Cerium dopant is present at about 0.5% or more.

34. The method of claim 32, wherein said Cerium dopant is present at about 5.0% by molar weight.

35. The method of claim 32, wherein said Cerium dopant is present at about 10% by molar weight.

36. The method of claim 32, wherein said Cerium dopant is present at about 20% by molar weight.

37. A method of localizing a positron annihilation event within a portion of a human body cross-section, the method comprising:
positioning the patient within a field of view of a positron emission tomography scanner system, the system comprising a scintillator comprising lutetium iodide ($LuI_3$) and trivalent cerium dopant;
detecting positron annihilation emissions from the patient using the positron emission tomography scanner system; and
generating patient image data in response to the detected emissions.

* * * * *